(12) United States Patent
Kashima et al.

(10) Patent No.: US 11,107,571 B2
(45) Date of Patent: Aug. 31, 2021

(54) INFORMATION PROCESSING APPARATUS, INFORMATION PROCESSING METHOD, PROGRAM, AND MEDICAL OBSERVATION SYSTEM

(71) Applicant: Sony Corporation, Tokyo (JP)

(72) Inventors: Koji Kashima, Kanagawa (JP); Takeshi Uemori, Tokyo (JP); Masahito Yamane, Kanagawa (JP); Tsuneo Hayashi, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/849,998

(22) Filed: Apr. 16, 2020

(65) Prior Publication Data

US 2020/0243185 A1    Jul. 30, 2020

Related U.S. Application Data

(63) Continuation of application No. 16/308,040, filed as application No. PCT/JP2017/015613 on Apr. 18, 2017, now Pat. No. 10,650,924.

(30) Foreign Application Priority Data

Jun. 16, 2016   (JP) ............................. JP2016-119687

(51) Int. Cl.
*A61B 90/20*    (2016.01)
*G16H 30/20*    (2018.01)
(Continued)

(52) U.S. Cl.
CPC ........... *G16H 30/20* (2018.01); *A61B 1/0005* (2013.01); *A61B 1/00006* (2013.01);
(Continued)

(58) Field of Classification Search
None
See application file for complete search history.

(56) References Cited

U.S. PATENT DOCUMENTS

| 10,650,924 B2 * | 5/2020 | Kashima .............. A61B 1/0005 |
| 2009/0023991 A1 | 1/2009 | Gono et al. |

(Continued)

FOREIGN PATENT DOCUMENTS

| CN | 101175433 A | 5/2008 |
| CN | 102770062 A | 11/2012 |

(Continued)

OTHER PUBLICATIONS

International Search Report dated Jul. 11, 2017 in PCT/JP2017/015613 filed on Apr. 18, 2017.

(Continued)

*Primary Examiner* — Eileen M Adams
(74) *Attorney, Agent, or Firm* — Xsensus LLP

(57) ABSTRACT

Provided is an medical information processing apparatus including processing circuitry that, based on surgical situation information concerning surgical characteristics at a time of observing an interior of a living body, selects at least one of a plurality of biological images each having a different wavelength range or at least one of secondary images generated from the plurality of biological images each having a different wavelength range, as a recommended image.

26 Claims, 12 Drawing Sheets

(51) Int. Cl.
*G16H 40/63* (2018.01)
*A61B 1/00* (2006.01)
*A61B 1/04* (2006.01)
*G16H 30/40* (2018.01)
*H04N 5/33* (2006.01)
*A61B 90/00* (2016.01)
*A61B 90/30* (2016.01)

(52) U.S. Cl.
CPC ...... *A61B 1/00009* (2013.01); *A61B 1/00039* (2013.01); *A61B 1/00045* (2013.01); *A61B 1/00186* (2013.01); *A61B 1/043* (2013.01); *A61B 90/20* (2016.02); *G16H 30/40* (2018.01); *G16H 40/63* (2018.01); *H04N 5/332* (2013.01); *A61B 90/30* (2016.02); *A61B 2090/373* (2016.02); *A61B 2090/378* (2016.02); *A61B 2090/3735* (2016.02)

(56) References Cited

U.S. PATENT DOCUMENTS

| | | | |
|---|---|---|---|
| 2010/0054576 A1 | 3/2010 | Tsujita | |
| 2010/0256449 A1 | 10/2010 | Kubo | |
| 2012/0088969 A1 | 4/2012 | Takahira et al. | |
| 2015/0010769 A1 | 1/2015 | Shih et al. | |
| 2015/0190061 A1* | 7/2015 | Godavarty | A61B 5/742 600/328 |
| 2016/0015473 A1* | 1/2016 | Frimer | A61B 1/00149 606/130 |
| 2019/0069836 A1* | 3/2019 | Hettrick | A61B 5/447 |

FOREIGN PATENT DOCUMENTS

| | | |
|---|---|---|
| CN | 103841876 A | 6/2014 |
| JP | 2011-177419 A | 9/2011 |
| JP | 2012-81087 A | 4/2012 |
| JP | 2013-085880 A | 5/2013 |
| JP | 2015-509744 A | 4/2015 |
| JP | 2016-007444 A | 1/2016 |
| WO | 2011/016428 A1 | 2/2011 |
| WO | 2012/035923 A1 | 3/2012 |
| WO | 2012/132790 A1 | 10/2012 |
| WO | 2013/051431 A1 | 4/2013 |
| WO | 2016/072237 A1 | 5/2016 |

OTHER PUBLICATIONS

Office Action dated Jun. 23, 2020, in corresponding Japanese patent Application No. 2016-119687, 16 pages.

* cited by examiner

FIG. 7

| | | TYPE OF RECOMMENDED IMAGE |
|---|---|---|
| SITUATION | SITUATION A | NEAR-INFRARED IMAGE |
| | SITUATION B | OXYGEN SATURATION-VISUALIZED IMAGE |
| | SITUATION C | FLUORESCENCE IMAGE |
| | SITUATION D | BLOOD VESSEL-HIGHLIGHTED IMAGE |
| | SITUATION E | SUPERIMPOSED IMAGE OF FLUORESCENCE IMAGE AND VISIBLE LIGHT IMAGE |
| | ⋮ | ⋮ |

RECOMMENDED IMAGE DATABASE

INFORMATION PROCESSING APPARATUS, INFORMATION PROCESSING METHOD, PROGRAM, AND MEDICAL OBSERVATION SYSTEM

CROSS REFERENCE TO RELATED APPLICATIONS

This application is a continuation of U.S. application Ser. No. 16/308,040, filed Dec. 7, 2018, which is based on PCT filing PCT/JP2017/015613, filed Apr. 18, 2017, and claims the benefit of Japanese Priority Patent Application JP 2016-119687, filed Jun. 16, 2016, the entire contents of each are incorporated herein by reference.

TECHNICAL FIELD

The present disclosure relates to an information processing apparatus, an information processing method, a program, and a medical observation system.

BACKGROUND ART

These days, various medical observation apparatuses such as medical endoscopes and medical microscopes are becoming used in the medical field. In particular, in the medical endoscope, as disclosed in PTL 1 below an attempted to, not only use a normal observation image in the visible light region, but also image an observation site by irradiation with light in specific wavelength ranges to generate spectral images in the specific wavelength ranges, and cause the spectral images to be displayed on a display screen is made.

CITATION LIST

Patent Literature

[PTL 1]
JP 2012-81087A

SUMMARY

Technical Problem

However, in a medical endoscope like that disclosed in PTL 1 above, the choice of an image that is caused to be displayed on a display screen depends on the decision by the manipulator of the medical endoscope; therefore, there is a case where, although there is a relatively appropriate image, the manipulator is not aware of this, and consequently the efficiency of working in endoscopic observation cannot be improved.

Furthermore, circumstances like the above may occur not only in observation with a medical endoscope but also in the case of working in observation with a medical microscope.

Thus, in view of the circumstances mentioned above, an embodiment of the present disclosure proposes an information processing apparatus, an information processing method, a program, and a medical observation system that can recommend a relatively appropriate vital observation image to the user during working using a medical observation apparatus.

Solution to Problem

According to an embodiment of the present disclosure, there is provided a medical information processing apparatus including: processing circuitry configured to, based on surgical situation information concerning surgical characteristics at a time of observing an interior of a living body, select at least one of a plurality of biological images each having a different wavelength range or at least one of secondary images generated from the plurality of biological images each having a different wavelength range, as a recommended image.

According to an embodiment of the present disclosure, there is provided a medical information processing method including: selecting, based on surgical situation information concerning surgical characteristics at a time of observing an interior of a living body, at least one of a plurality of biological images each having a different wavelength range or at least one of secondary images generated from the plurality of biological images each having a different wavelength range, as a recommended image.

According to an embodiment of the present disclosure, there is provided a non-transitory computer readable medium having stored therein a program that when executed by a computer causes the computer to execute a medical information processing method, including: selecting, based on surgical situation information concerning surgical characteristics at a time of observing an interior of a living body, at least one of a plurality of biological images each having a different wavelength range or at least one of secondary images generated from the plurality of biological images each having a different wavelength range, as a recommended image.

According to an embodiment of the present disclosure, there is provided a medical observation system including: a medical observation apparatus including first processing circuitry configured to generate a plurality of biological images by capturing images of an interior and exterior of a living body in a plurality of wavelength ranges, and an information processing apparatus including second processing circuitry configured to, based on surgical situation information concerning surgical characteristics at a time of observing the interior of the living body, select at least one of the plurality of biological images having different wavelength ranges or at least one of secondary images generated from the plurality of biological images, as a recommended image.

Advantageous Effects of Invention

As described above, according to an embodiment of the present disclosure, a relatively appropriate vital observation image can be recommended to the user during working using a medical observation apparatus.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 7 is an illustration diagram for describing a recommended image database included in the information processing apparatus according to the embodiment.

DESCRIPTION OF EMBODIMENTS

Figure 1:
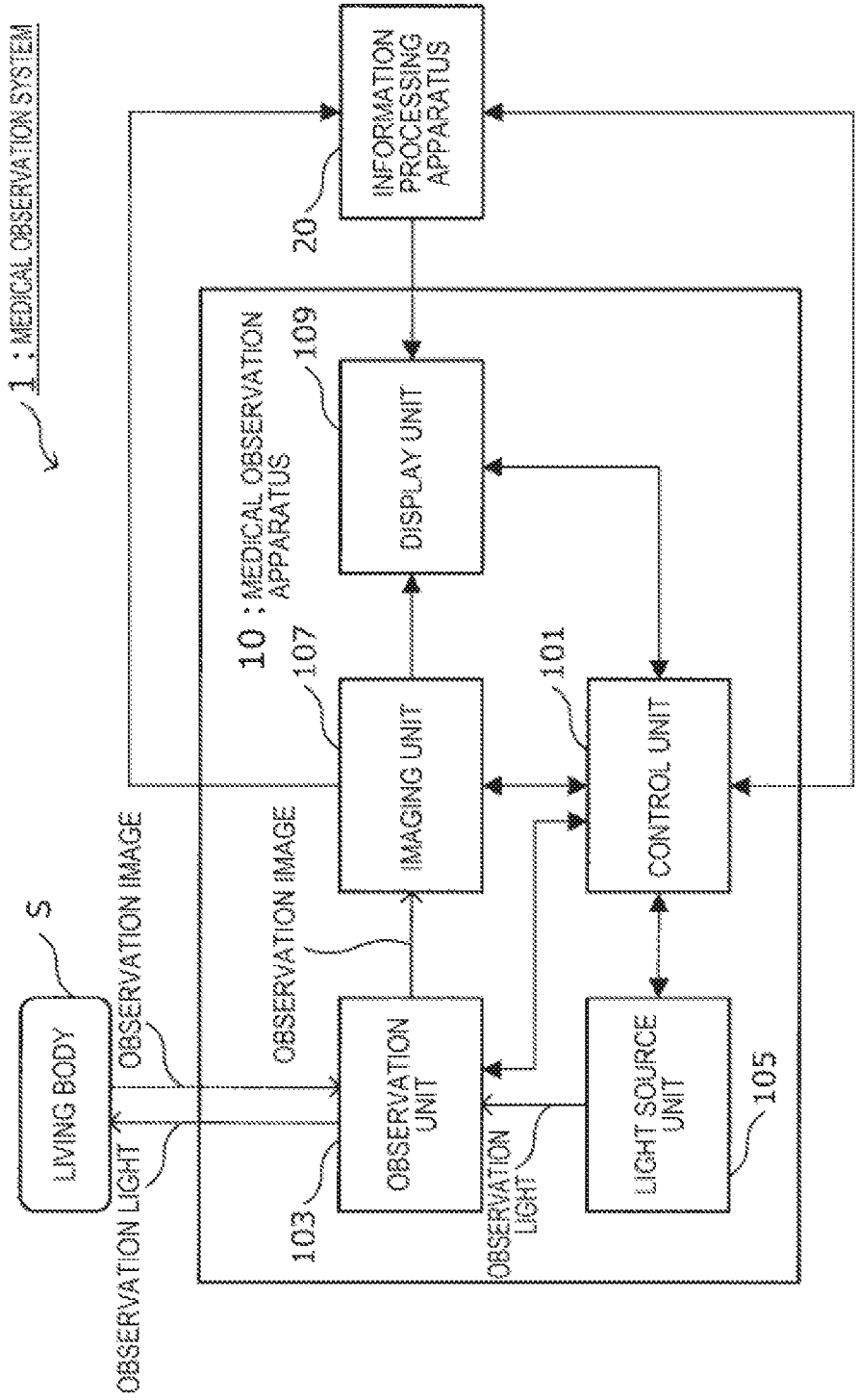
FIG. 1 is an illustration diagram schematically showing an overall configuration of a medical observation system according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

The description is given in the following order.
1. Embodiment
1.1. With regard to overall configuration of medical observation system
1.2. With regard to configuration of medical observation apparatus
1.3. With regard to configuration of information processing apparatus
1.4. With regard to information processing method
1.5. With regard to hardware configuration Embodiment <With Regard to Overall Configuration of Medical Observation System>

First, the overall configuration of a medical observation system 1 according to an embodiment of the present disclosure is briefly described with reference to FIG. 1. FIG. 1 is an illustration diagram schematically showing the overall configuration of the medical observation system 1 according to the present embodiment.

As shown in FIG. 1, the medical observation system 1 according to the present embodiment includes a medical observation apparatus 10 for observing the interior of a living body and an information processing apparatus 20.

The medical observation apparatus 10 is a medical apparatus that observes the interior of a living body S by a part of the medical observation apparatus 10 being inserted into the interior of the living body S or placed near an internal organ of the living body S. Examples of the medical observation apparatus 10 like this include various endoscope apparatuses such as rigid endoscopes, flexible endoscopes, and arthroscopes, and various microscope apparatuses.

The medical observation apparatus 10 according to the present embodiment applies predetermined observation light to a part of the living body S that is an object to be observed and images the part of the living body S irradiated with observation light, and thereby generates a plurality of biological images including a captured image of the living body in the visible light region (a region falling under the wavelength range of approximately 400 nanometers to 800 nanometers).

The biological images may include, in addition to the captured image of the living body in the visible light region mentioned above, captured images of the living body in various wavelength ranges such as a captured image of the living body in the near-infrared region (a region falling under the wavelength range of approximately 800 nanometers to approximately 2.5 micrometers) and a captured image of the living body in the ultraviolet region, for example. Further, the biological images may include other captured images of the living body such as an image in the case where the living body is observed using ultrasonic waves and an image in the case where the living body is observed by optical coherence tomography (OCT), for example.

The plurality of biological images including a captured image of the living body in the visible light region that are generated by the medical observation apparatus 10 are displayed at any time on a display device such as a display connected to the medical observation apparatus 10 via wire or wirelessly, and are outputted to the information processing apparatus 20 according to the present embodiment described in detail later.

A specific configuration of the medical observation apparatus 10 is described later.

The information processing apparatus 20 according to the present embodiment analyzes captured images generated by the medical observation apparatus 10 and decides on an image relatively appropriate for working as a recommended image, and recommends the recommended image to the user of the medical observation apparatus 10 (for example, a doctor performing an operation or others). Thereby, in the information processing apparatus 20 according to the present embodiment, the situation at the time when the user observes the interior of the living body can be grasped, and an observation image in accordance with the situation can be recommended as a recommended image to the user of the medical observation apparatus 10. As a result, the user of the medical observation apparatus 10 can be aware that there is an image that can be a relatively appropriate observation image in terms of the continuation of ongoing working, and the efficiency of working with the medical observation apparatus can be improved.

A specific configuration of the information processing apparatus 20 is described later.

Although in FIG. 1 the case where the medical observation apparatus 10 and the information processing apparatus 20 according to the present embodiment exist as different apparatuses is described, the function of the information processing apparatus 20 described in detail later may be achieved as one function of the medical observation apparatus 10, as a matter of course.

<With Regard to Configuration of Medical Observation Apparatus 10>

Next, a specific configuration of the medical observation apparatus 10 according to the present embodiment is briefly described with reference to FIG. 1 to FIG. 2C. FIG. 2A to FIG. 2C are illustration diagrams schematically showing examples of the imaging unit included in the medical observation apparatus according to the present embodiment.

As mentioned above, the medical observation apparatus 10 according to the present embodiment is a medical apparatus that observes the interior of the living body S by a part of the medical observation apparatus 10 being inserted into the interior of the living body S or placed near an internal organ of the living body S.

As schematically shown in FIG. 1, the medical observation apparatus 10 mainly includes a control unit 101, an observation unit 103, a light source unit 105, an imaging unit 107, and a display unit 109.

The control unit 101 is formed of, for example, a central processing unit (CPU), a read-only memory (ROM), a random access memory (RAM), etc. The control unit 101 is a unit that comprehensively controls the overall function of the medical observation apparatus 10, and collectively controls the operating states of the observation unit 103, the light source unit 105, the imaging unit 107, and the display unit 109 included in the medical observation apparatus 10. The control unit 101 is, for example, a unit corresponding to a camera control unit (CCU) of a medical endoscope apparatus or a medical microscope apparatus. Further, the control unit 101 can output, at an arbitrary timing to the information processing apparatus 20 according to the present embodiment, a variety of information such as information concerning setting conditions that are set for each of the units constituting the medical observation apparatus 10 and information concerning the operating state of each of the units constituting the medical observation apparatus 10.

The observation unit 103 is a unit of which a part is inserted into the interior of the living body S or placed near an internal organ of the living body S under the control by the control unit 101. The observation unit 103 causes an observation image of the interior of the living body S observed using observation light applied from the light source unit 105 to form an image on the imaging unit 107 in a later stage. The observation unit 103 corresponds to, for example, an endoscope unit in a medical endoscope apparatus or a microscope unit in a medical microscope apparatus. The observation unit 103 according to the present embodiment is not particularly limited, and known endoscope units, microscope units, and the like may be used.

The light source unit 105 is a unit that emits observation light for observing the interior of the living body under the control by the control unit 101, and is optically connected to the observation unit 103. The light source unit 105 includes at least a visible light source (for example, a white light source or the like) for obtaining a captured image of the living body in the visible light region. The light source unit 105 may include not only such a visible light source but also various known light sources such as a near-infrared light source for obtaining a captured image of the living body in the near-infrared region, an ultraviolet light source, and various laser light sources that emit specific types of visible light. The light source unit 105 can, under the control by the control unit 101, switch the type of observation light emitted from these various light sources at an arbitrary timing. The light source unit 105 may include not only light sources like the above but also a light source for achieving a specific function, such as a light source for OCT or a light source for distance measurement.

The imaging unit 107 is a unit that, under the control by the control unit 101, captures an observation image of the interior of the living body S based on observation light from the light source unit 105 and generates image data of a plurality of biological images including a captured image of the living body in the visible light region. The imaging unit 107 is optically connected to the observation unit 103. The imaging unit 107 according to the present embodiment performs imaging while distinguishing various types of observation light (for example, some types of light in various wavelength ranges such as visible light, near-infrared light, and ultraviolet light) from each other, and thereby generates image data of a plurality of biological images.

In a common medical observation system, an image close to a situation of direct observation with the human eye is captured by using an imaging element having sensitivity at wavelengths in the visible light region and the image is appropriately developed, and the observation result is displayed on a display device as a normal observation image. Further, in a common medical observation system that can perform special light observation, in many cases various functions are achieved, such as, in addition to a normal observation mode in which a captured image in the visible light region is displayed, a fluorescence observation mode in which fluorescence occurring in the living body is observed using an imaging element having sensitivity also at a wavelength in the near-infrared region and a narrow wavelength image (narrow band imaging, NBI) observation mode in which a plurality of specific narrow wavelengths are combined to facilitate the distinction between blood vessels at different depths from the surface of the skin.

However, special light observation like the above is enabled by combining an illumination apparatus that selectively applies light of a specific wavelength and an optical filter that transmits or reflects light of a specific wavelength, and is therefore difficult to perform simultaneously with the normal observation mode of visible light.

Figure 2A:
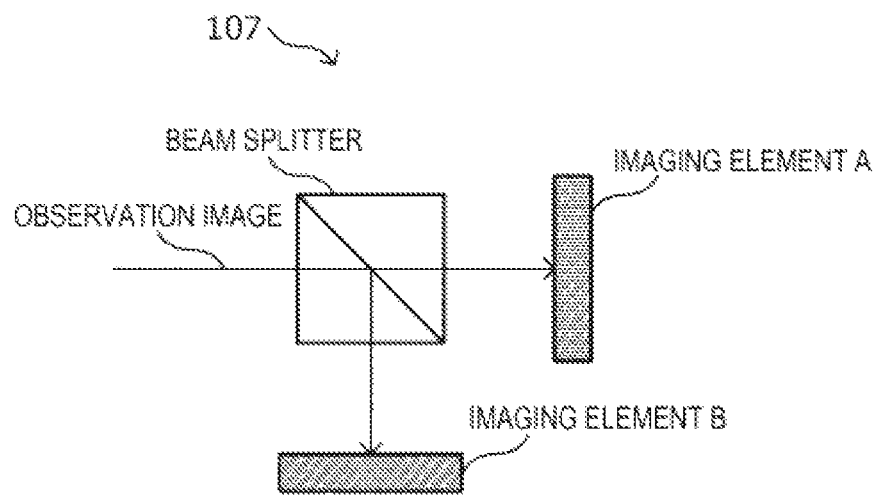
FIG. 2A is an illustration diagram schematically showing an example of an imaging unit included in the medical observation apparatus according to the embodiment.
Figure 2B:
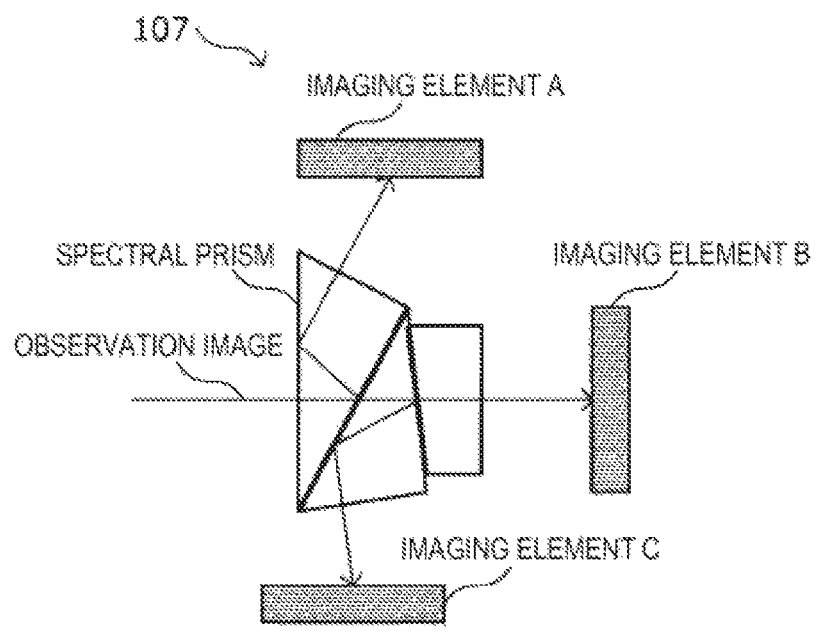
FIG. 2B is an illustration diagram schematically showing an example of the imaging unit included in the medical observation apparatus according to the embodiment.
Figure 2C:
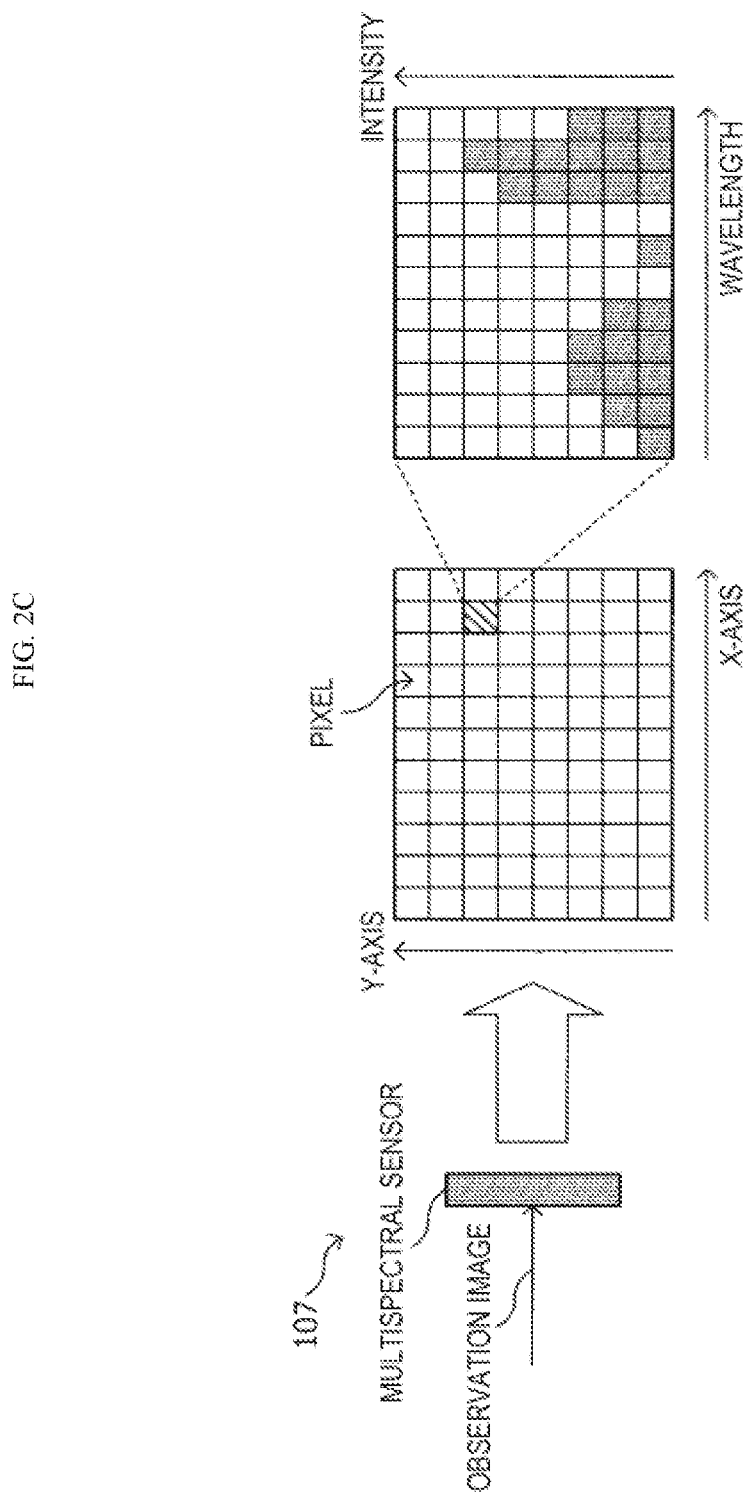
FIG. 2C is an illustration diagram schematically showing an example of the imaging unit included in the medical observation apparatus according to the embodiment.

Thus, in the medical observation apparatus 10 according to the present embodiment, the imaging unit 107 like those shown in FIG. 2A to FIG. 2C is provided, and thereby a captured image of the living body in the visible light region and other captured images of the living body can be acquired simultaneously.

The imaging unit 107 may be, for example as shown in FIG. 2A, one including any of various beam splitters such as a normal beam splitter and a polarizing beam splitter and two types of imaging elements of an imaging element A and an imaging element B. In the case of the imaging unit 107 like that shown in FIG. 2A, an observation image from the observation unit 103 is branched into two optical paths by the beam splitter, and forms an image on each of the imaging element A and the imaging element B. Here, for example, an imaging element for visible light having sensitivity to light in the visible light region may be used as the imaging element A and an imaging element for near-infrared light having sensitivity to light in the near-infrared region may be used as the imaging element B; thereby, a captured image of the living body in the visible light region and a captured image of the living body in the near-infrared region can be generated. Further, another known imaging element may be used as the imaging element B, and thereby various captured images of the living body can be generated as well as a captured image of the living body in the visible light region.

Although in FIG. 2A the case where one beam splitter is used is shown, two or more beam splitters may be used in combination, and thereby an observation image can be branched into a larger number of optical paths and a larger number of types of captured images of the living body can be captured simultaneously.

Further, the imaging unit 107 may be, for example as shown in FIG. 2B, one including a spectral prism in which a plurality of (in FIG. 2B, three) optical prisms are joined to each other and a plurality of types of imaging elements (in FIG. 2B, three types of an imaging element A to an imaging element C). In the case of the imaging unit 107 like that shown in FIG. 2B, the joint surface between adjacent optical prisms may be made to function as one of a beam splitter, a polarizing beam splitter, and a wavelength selection filter, and thereby an observation image from the observation unit 103 can be branched into a plurality of optical paths (in the case of FIG. 2B, three optical paths).

The observation image from the observation unit 103 is branched into a plurality of optical paths by the spectral prism, and forms an image on each imaging element provided at the end of each optical path. Here, for example, an imaging element for visible light having sensitivity to light in the visible light region may be used as the imaging element A and an imaging element for near-infrared light having sensitivity to light in the near-infrared region may be used as the imaging element B; thereby, a captured image of the living body in the visible light region and a captured image of the living body in the near-infrared region can be generated. Further, another known imaging element may be provided in the position of the imaging element C as necessary, and thereby various captured images of the living body can be generated as well as a captured image of the living body in the visible light region and a captured image of the living body in the near-infrared region.

In a spectral prism like that shown in FIG. 2B, the number of optical prisms used may be increased, and thereby an observation image can be branched into a still larger number of optical paths, and a larger number of types of captured images of the living body can be simultaneously captured.

Further, the imaging unit 107 may be, as shown in FIG. 2C, one including what is called a multispectral sensor. As schematically shown in FIG. 2C, the multispectral sensor is a two-dimensional image sensor including at least a pixel that detects the intensities of light in a plurality of wavelength ranges at one time while distinguishing them for each wavelength range. By using such a multispectral sensor, multispectral data that are the intensities of light in a plurality of narrow wavelength ranges can be acquired in one pixel of the image.

It is preferable that all the pixels included in a multispectral sensor like that schematically shown in FIG. 2C be a pixel that detects the intensities of light in a plurality of wavelength ranges at one time while distinguishing them for each wavelength range, but it is not necessary that all the pixels be a pixel like the above that detects the intensities of light in a plurality of wavelength ranges at one time while distinguishing them for each wavelength range. This is because, by performing various known interpolation processings using the output from a pixel like the above that detects the intensities of light in a plurality of wavelength ranges at one time while distinguishing them for each wavelength range, the intensities of light in a plurality of wavelength ranges can be calculated for each wavelength range even in the position of a pixel that does not have a function like the above.

By using a multispectral sensor like that shown in FIG. 2C, the imaging unit 107 can be made smaller in size than the imaging unit 107 like those shown in FIG. 2A and FIG. 2B, and the medical observation apparatus 10 can be further downsized.

The imaging unit 107 may be configured such that a beam splitter or a spectral prism like that shown in FIG. 2A or FIG. 2B and a multispectral sensor like that shown in FIG. 2C are combined with each other and thereby a larger number of types of biological images are generated, as a matter of course.

For various biological images generated by the imaging unit 107 like, for example, those shown in FIG. 2A to FIG. 2C, an appropriate image is selected by appropriate control performed by the control unit 101 in accordance with the user manipulation by the user of the medical observation apparatus 10, and is displayed on a display screen provided in the display unit 109 in a later stage. The user of the medical observation apparatus 10 usually focuses attention on a captured image of the living body in the visible light region as an observation image of the interior of the living body; thus, in many cases mainly a captured image of the living body in the visible light region is displayed on the display screen of the display unit 109 in a later stage.

The imaging unit 107 outputs a plurality of biological images generated in the above manner to the information processing apparatus 20 according to the present embodiment at any time under the control of the control unit 101.

There may be a case where the number of imaging elements included in the imaging unit 107 according to the present embodiment is only one, such as a case where the imaging unit 107 includes only one imaging element having sensitivity in the visible light region to the near-infrared region. Even in such a case, the light source unit 105 and the imaging unit 107 may, in cooperation with each other under the control of the control unit 101, perform imaging while switching the wavelength range of light that forms an image on the imaging element; thereby, biological images in a plurality of wavelength ranges can be generated.

The display unit 109 is a unit that displays at least one of the plurality of biological images generated by the imaging unit 107 to the user of the medical observation apparatus 10 under the control by the control unit 101. The number of display screens provided in the display unit 109 is not particularly limited, and the display unit 109 may include only one display screen or may include a plurality of display screens. The display unit 109 is not particularly limited, and a known display unit 109 may be used.

Further, information concerning a recommended image recommended by the information processing apparatus 20 described later is displayed on the display screen of the display unit 109 according to the present embodiment as appropriate.

In the above, an example of the configuration of the medical observation apparatus 10 according to the present embodiment is briefly described with reference to FIG. 1 to FIG. 2C. The medical observation apparatus 10 according to the present embodiment may include, in addition to various units like those shown in FIG. 1, various other units such as an ultrasonic wave oscillation apparatus and an ultrasonic wave detection unit, for example.

<With Regard to Configuration of Information Processing Apparatus 20>

Next, the information processing apparatus 20 according to the present embodiment is described in detail with reference to FIG. 3 to FIG. 9.

Figure 3:
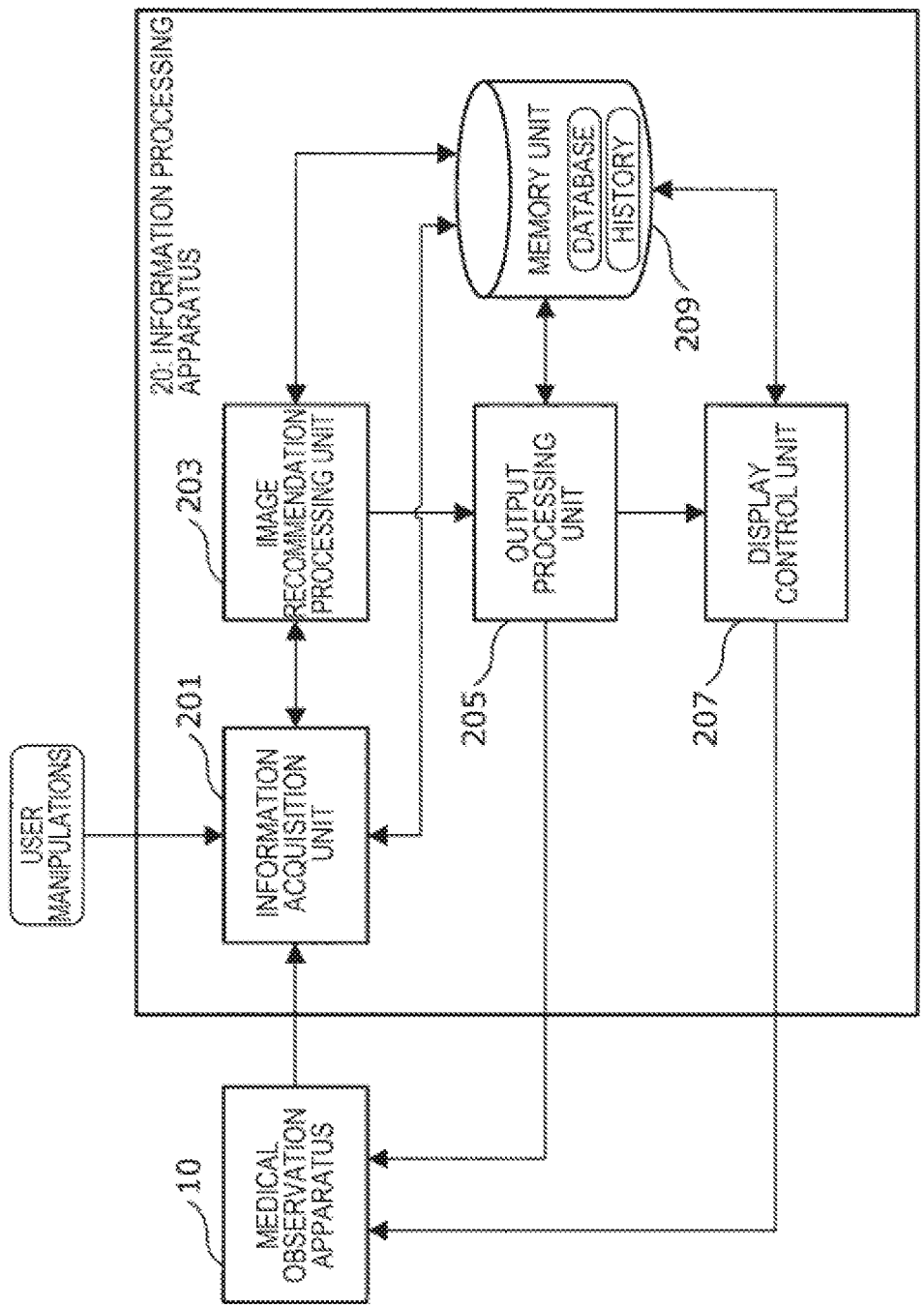
FIG. 3 is a block diagram schematically showing an example of a configuration of an information processing apparatus according to the embodiment.
Figure 4:
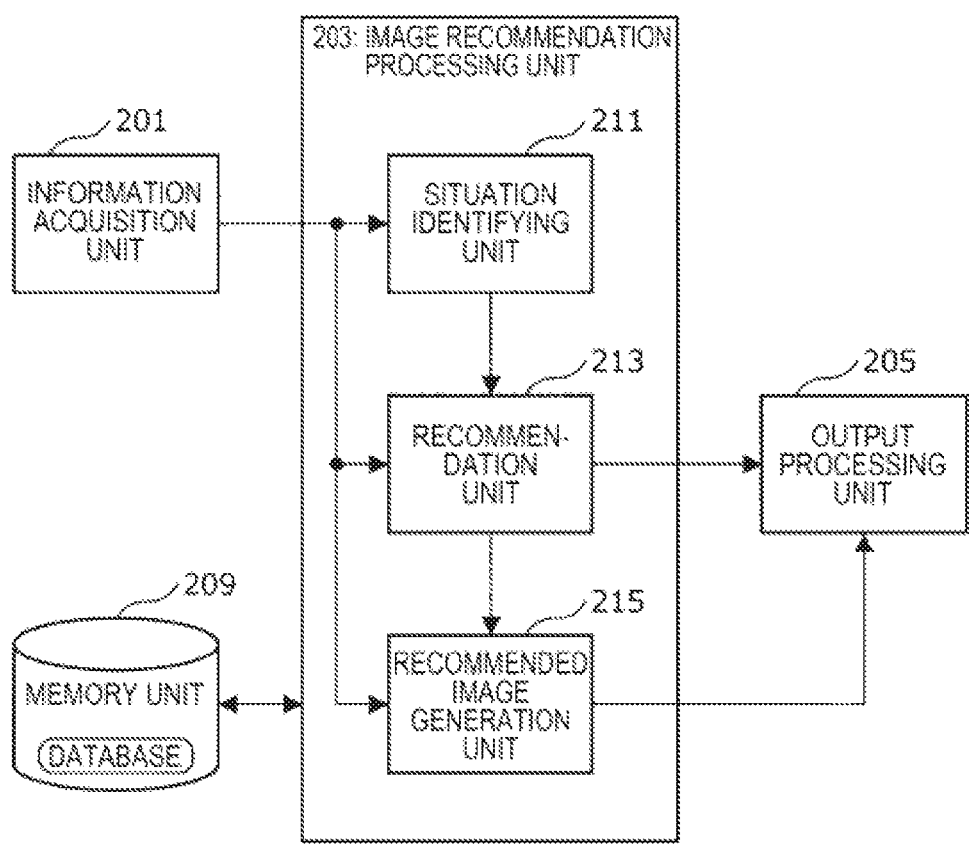
FIG. 4 is a block diagram schematically showing an example of a configuration of an image recommendation processing unit included in the information processing apparatus according to the embodiment.
Figure 5:
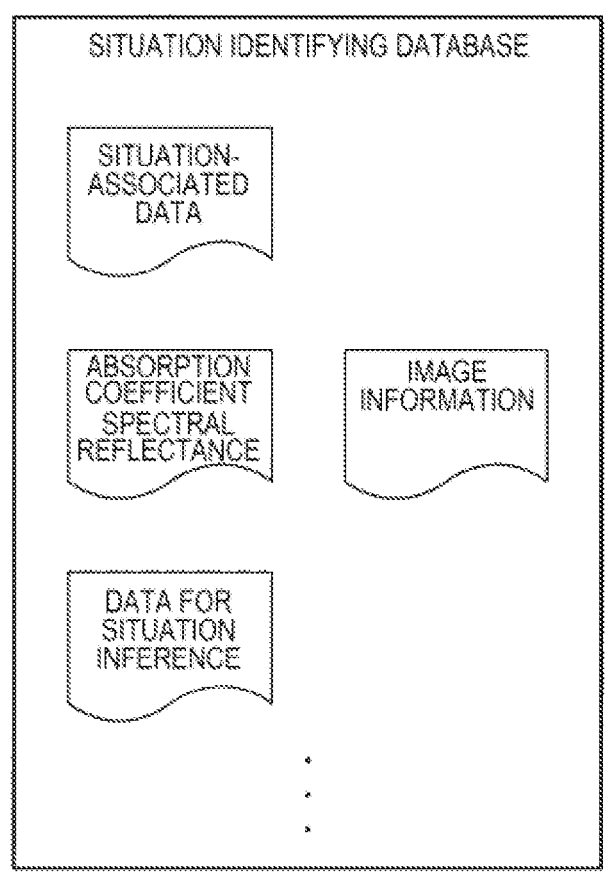
FIG. 5 is an illustration diagram for describing a situation identifying database included in the information processing apparatus according to the embodiment.
Figure 6:
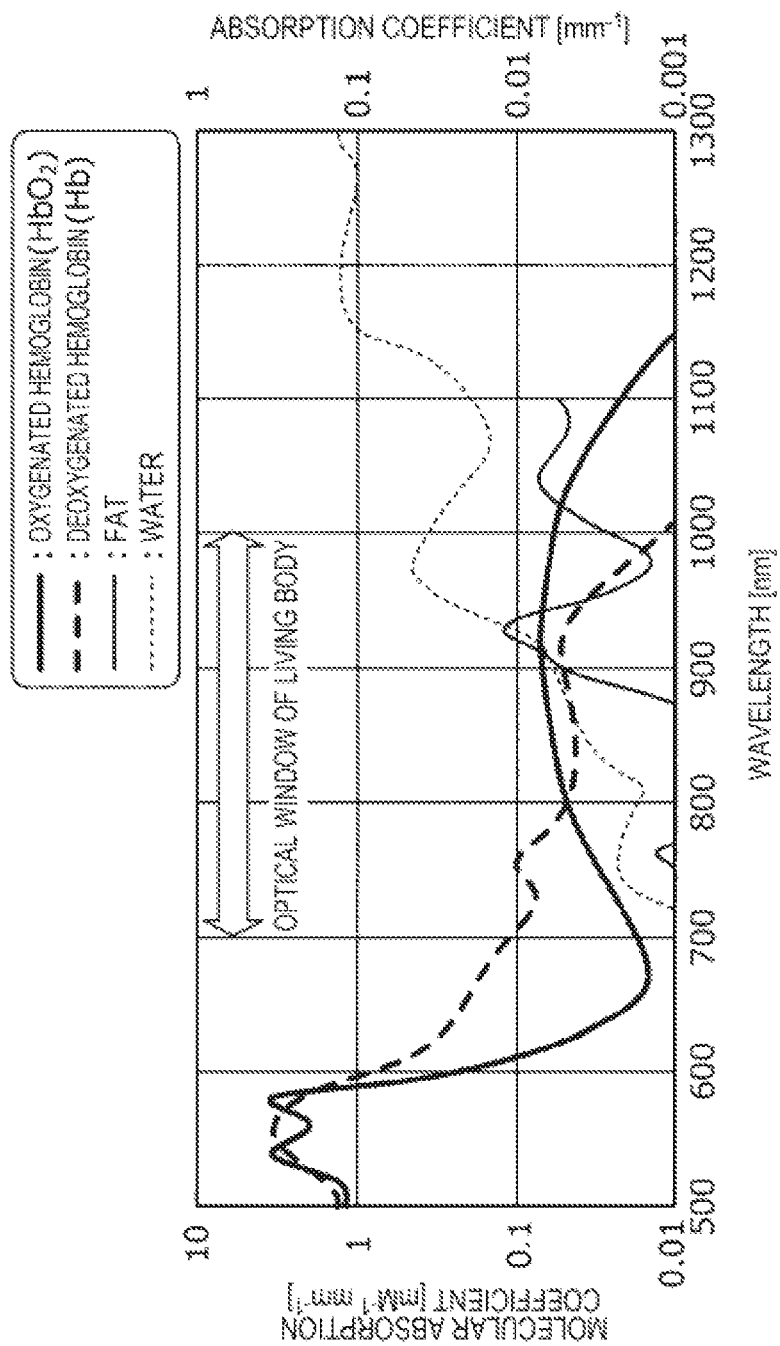
FIG. 6 is an illustration diagram showing an example of an absorption spectrum of main substances in a living tissue.
Figure 8:
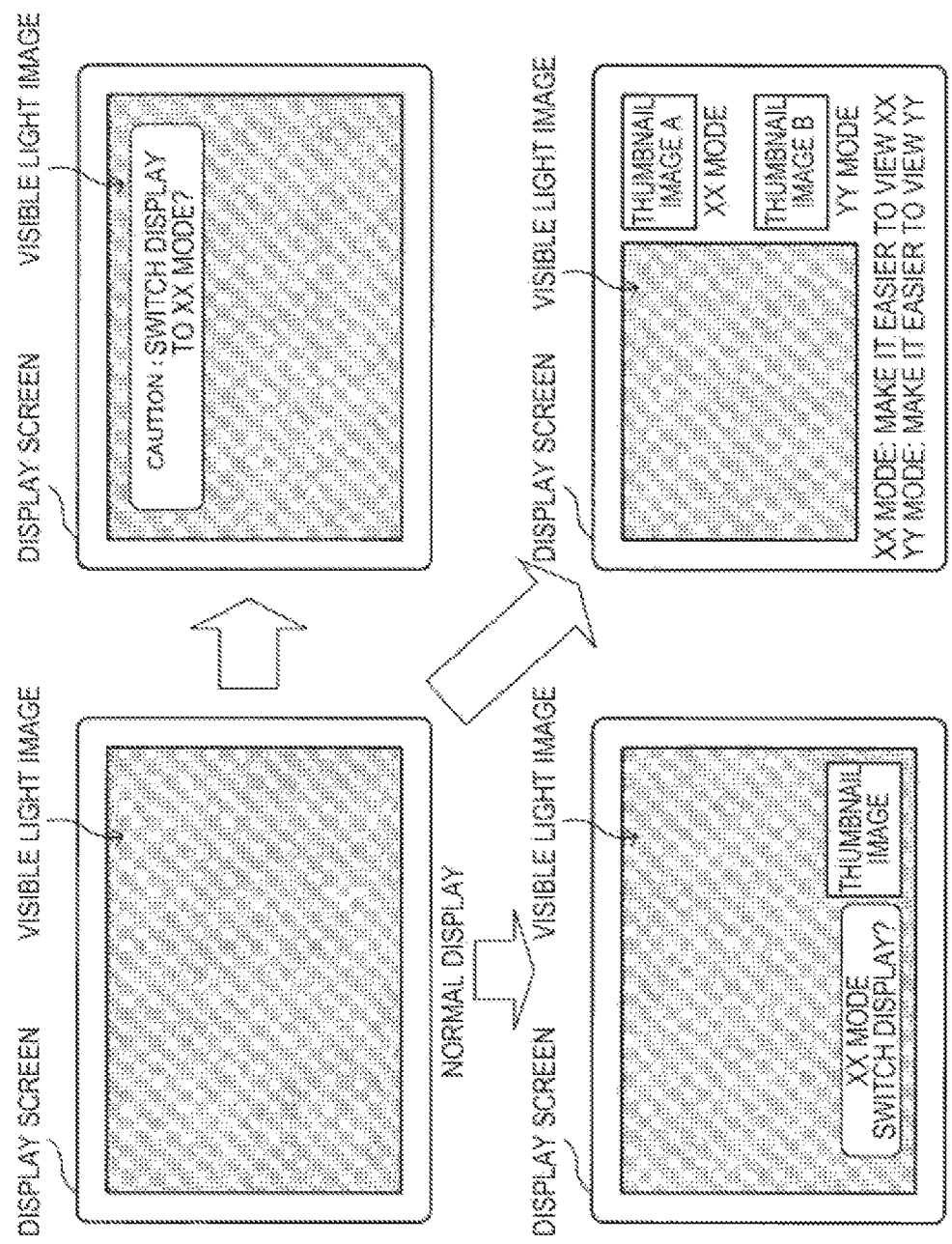
FIG. 8 is an illustration diagram schematically showing examples of a display screen in the information processing apparatus according to the embodiment.
Figure 9:
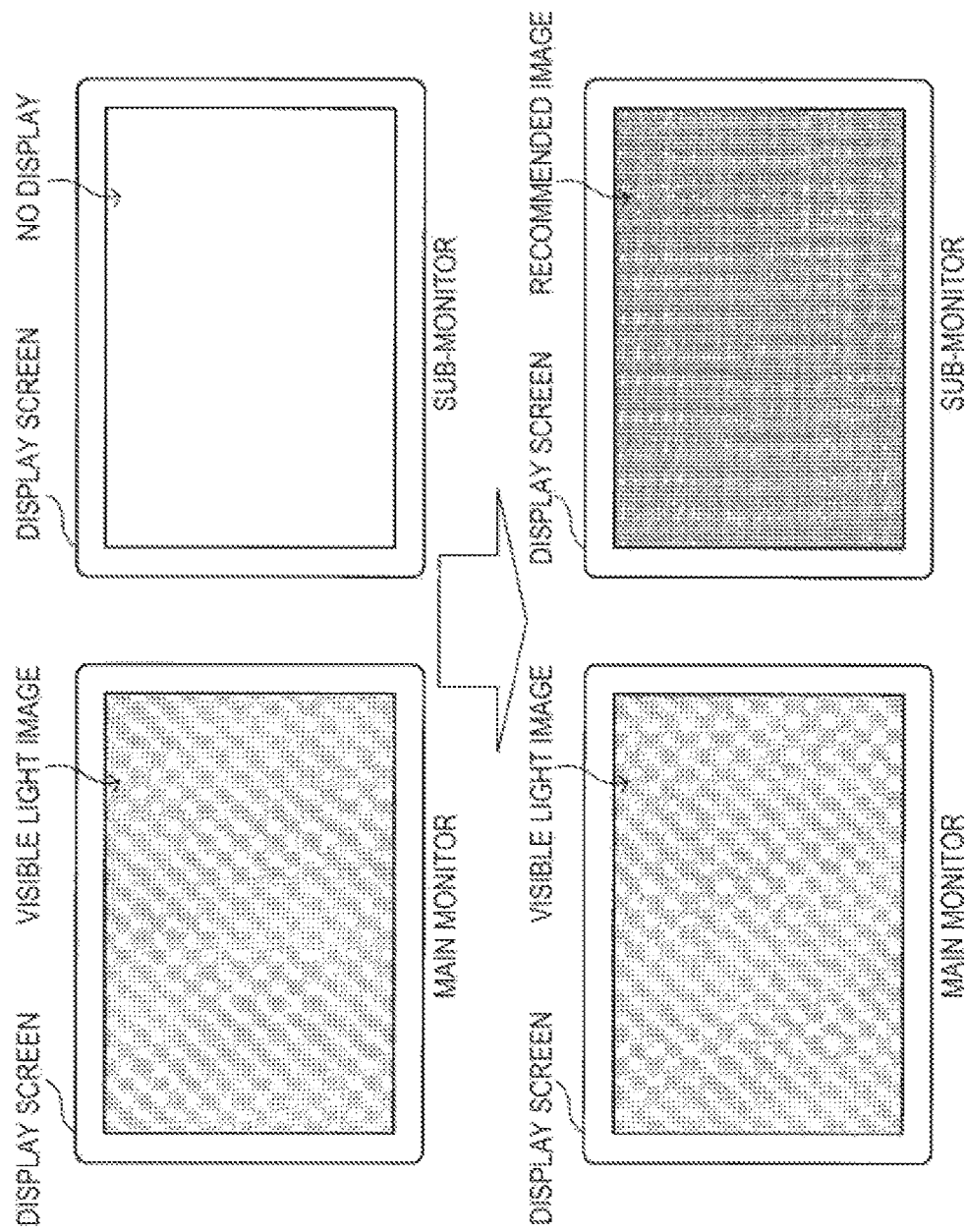
FIG. 9 is an illustration diagram schematically showing examples of the display screen in the information processing apparatus according to the embodiment.

FIG. 3 is a block diagram schematically showing an example of the configuration of the information processing apparatus according to the present embodiment. FIG. 4 is a block diagram schematically showing an example of the configuration of an image recommendation processing unit included in the information processing apparatus according to the present embodiment. FIG. 5 is an illustration diagram for describing a situation identifying database included in the information processing apparatus according to the present embodiment, and FIG. 6 is an illustration diagram showing an example of the absorption spectrum of main substances in a living tissue. FIG. 7 is an illustration diagram for describing a recommended image database included in the information processing apparatus according to the present embodiment. FIG. 8 and FIG. 9 are illustration diagrams schematically showing examples of the display screen in the information processing apparatus according to the present embodiment.

With Regard to Overall Configuration of Information Processing Apparatus 20

As mentioned above, the information processing apparatus 20 according to the present embodiment is an apparatus that analyzes captured images generated by the medical observation apparatus 10 to decide on an image relatively appropriate for working as a recommended image and that recommends the recommended image to the user of the medical observation apparatus 10. As schematically shown in FIG. 3, the information processing apparatus 20 mainly includes an information acquisition unit 201, an image recommendation processing unit 203, an output processing unit 205, a display control unit 207, and a memory unit 209.

The information acquisition unit 201 is form of, for example, a CPU, a ROM, a RAM, a communication device, etc. The information acquisition unit 201 acquires a variety of information from the medical observation apparatus 10. For example, the information acquisition unit 201 acquires, at any time, image data of a plurality of biological images including a captured image of the living body in the visible light region that are generated by the medical observation apparatus 10. Further, the information acquisition unit 201 can acquire a variety of information concerning the medical observation apparatus 10 from the medical observation apparatus 10 (more specifically, the control unit 101 etc. of the medical observation apparatus 10). Further, the information acquisition unit 201 can acquire, from the medical observation apparatus 10, information concerning the usage situation of recommended images, such as the result of the user's choice regarding images recommended by the information processing apparatus 20 according to the present embodiment. Further, the information processing apparatus 20 according to the present embodiment can also acquire information concerning various user manipulations made by the user of the medical observation apparatus 10, the manipulator of the information processing apparatus 20, or others.

Here, examples of the variety of information concerning the medical observation apparatus 10 include setting information concerning various settings of the medical observation apparatus 10, characteristic information concerning the characteristics of the medical observation apparatus 10, operating information concerning the operating state of the medical observation apparatus 10 and various peripheral devices cooperating with the medical observation apparatus 10, etc. Examples of the setting information concerning various settings of the medical observation apparatus 10 include the setting information of the light source unit 105 in the medical observation apparatus 10 (for example, information concerning the wavelength of observation light), the information of what type of peripheral device cooperates with the medical observation apparatus 10, etc. Examples of the characteristic information concerning the characteristics of the medical observation apparatus 10 include setting information concerning the sensor spectral characteristics of the imaging unit 107 in the medical observation apparatus 10, etc. Examples of the operating information concerning the operating state of the medical observation apparatus 10 and various peripheral devices cooperating with the medical observation apparatus 10 include what type of light source is in operation as the light source unit 105, the operating situation of an energy device such as an electric scalpel, the operating situation of a smoke extraction apparatus for discharging mist and smoke existing in the body cavity to the outside of the body, etc.

On acquiring image data concerning a plurality of biological images from the medical observation apparatus 10, the information acquisition unit 201 outputs the acquired image data to the image recommendation processing unit 203 described later. The information acquisition unit 201 may associate time information concerning the date and time of the acquisition of image data etc. with the acquired image data, and may record the image data as history information in the memory unit 209 described later.

Further, on the basis of information concerning the usage situation of recommended images acquired from the medical observation apparatus 10, the information acquisition unit 201 may record the usage history of recommended images in the memory unit 209 described later.

On acquiring a variety of information concerning the medical observation apparatus 10 like the above from the medical observation apparatus 10, the information acquisition unit 201 outputs the acquired variety of information to the image recommendation processing unit 203 described later. The variety of information concerning the medical observation apparatus 10 may be notified from the control unit 101 of the medical observation apparatus 10 every time when image data of a plurality of biological images are outputted to the information processing apparatus 20. Instead of every time when image data are outputted, the control unit 101 of the medical observation apparatus 10 may notify a variety of information concerning the medical observation apparatus 10 at the timing when the content of any piece of information is changed.

The image recommendation processing unit 203 is formed of, for example, a CPU, a ROM, a RAM, etc. The image recommendation processing unit 203 is a processing unit that uses image data and a variety of information acquired by the information acquisition unit 201 to decide on a recommended image in accordance with the situation at the time point when the interior of the living body is observed, and that performs image recommendation processing that recommends the recommended image to the user of the medical observation apparatus 10. The image recommendation processing unit 203 includes at least a recommendation unit that, on the basis of a plurality of biological images and situation information concerning the situation at the time of observing the interior of the living body or the surgical situation information concerning surgical characteristics at a time of observing an interior of a living body, decides on at least one of the plurality of biological images or at least one of images generated from the plurality of biological images as a recommended image in accordance with the situation mentioned above.

A specific configuration of the image recommendation processing unit 203 is described later.

On deciding on, using a plurality of biological images, a recommended image in accordance with the situation at the time point when the interior of the living body is observed, the image recommendation processing unit 203 outputs information concerning the decided on recommended image to the output processing unit 205 in a later stage. The image recommendation processing unit 203 may associate time information concerning the date and time of obtainment of a processing result regarding the decided on recommended image etc. with the processing result, and may store the processing result as history information in the memory unit 209 in a later stage.

The output processing unit 205 is formed of, for example, a CPU, a ROM, a RAM, am output device, a communication device, etc. The output processing unit 205 outputs a processing result regarding the decided on recommended image outputted from the image recommendation processing unit 203 to the medical observation apparatus 10. The control unit 101 of the medical observation apparatus 10 that has acquired the processing result may cause the acquired processing result to be displayed on the display unit 109, and can thereby recommend an observation image of the living body in accordance with the situation to the user of the medical observation apparatus 10. The output processing unit 205 may output the processing result directly to the display unit 109 of the medical observation apparatus 10 in cooperation with the display control unit 207 in a later stage.

The output processing unit 205 may output the processing result regarding the recommended image outputted from the image recommendation processing unit 203 as a printed matter, or may output the processing result as data to an external information processing apparatus, server, etc.

The display control unit 207 is formed of, for example, a CPU, a ROM, a RAM, an output device, a communication device, etc. The display control unit 207 performs display control at the time of displaying various results outputted from the output processing unit 205 on an output device such as a display included in the information processing apparatus 20, an output device provided outside an arithmetic processing device 200 (for example, the display unit 109 of the medical observation apparatus 10), or the like. Thereby, the user of the medical observation apparatus 10 can grasp various results on the spot.

The memory unit 209 is an example of the memory device included in the information processing apparatus 20, and is formed of a RAM, a storage device, etc. included in the information processing apparatus 20. Various databases used when the information processing apparatus 20 according to the present embodiment performs image recommendation processing described in detail later are recorded in the memory unit 209. Further, a variety of history information related to image recommendation processing described in detail later may be recorded in the memory unit 209. Further, various parameters, situations of a certain processing still in progress, etc. that have to be saved when the information processing apparatus 20 according to the present embodiment performs the processing, or various databases, programs, etc. are recorded in the memory unit 209 as appropriate. The information acquisition unit 201, the image recommendation processing unit 203, the output processing unit 205, the display control unit 207, etc. can freely perform read/write processing on the memory unit 209.

With Regard to Configuration of Image Recommendation Processing Unit 203

Next, the configuration of the image recommendation processing unit 203 included in the information processing apparatus 20 according to the present embodiment is described in detail with reference to FIG. 4 to FIG. 7.

As mentioned above, the image recommendation processing unit 203 according to the present embodiment uses image data and a variety of information acquired by the information acquisition unit 201 to decide on a recommended image in accordance with the situation at the time point when the interior of the living body is observed, and performs image recommendation processing that recommends the recommended image to the user of the medical observation apparatus 10. As schematically shown in FIG. 4, the image recommendation processing unit 203 includes a situation identifying unit 211, a recommendation unit 213, and a recommended image generation unit 215.

The situation identifying unit 211 is formed of, for example, a CPU, a ROM, a RAM, etc. The situation identifying unit 211 is a processing unit that identifies the situation at the time when the interior of the living body is observed on the basis of a plurality of biological images outputted from the medical observation apparatus 10. More specifically, the situation identifying unit 211 identifies the situation at the time when the interior of the living body is observed on the basis of at least one of the following pieces of information acquired by the information acquisition unit 201: setting information concerning the setting of the medical observation apparatus 10, characteristic information concerning the characteristics of the medical observation apparatus 10, operating information concerning the operating state of the medical observation apparatus 10 and peripheral devices cooperating with the medical observation apparatus 10, a biological image, and secondary information generated on the basis of a biological image.

The secondary information mentioned above generated on the basis of a biological image is not particularly limited, and any information may be used to the extent that it is information secondarily calculated by performing various image processings or information processings on a biological image. Examples of the secondary information include information concerning the spectral reflectance or the absorption coefficient of an organ and a biological substance existing in the interior of the living body that can be calculated by focusing attention on a captured image of the living body in a certain wavelength range, information concerning the oxygen saturation of blood, information concerning a recognition result obtained by performing image recognition processing on a biological image using image information concerning an organ existing in the interior of the living body and a medical instrument used for medical practice, etc.

More specifically, it is preferable that the situation identifying unit 211 identify the situation at the time when the interior of the living body is observed with reference to a situation identifying database in which at least one of setting information concerning the setting of the medical observation apparatus 10, characteristic information concerning the characteristics of the medical observation apparatus 10, operating information concerning the operating state of the medical observation apparatus 10 and peripheral devices cooperating with the medical observation apparatus 10, a biological image, and secondary information generated on the basis of a biological image, and the situation at the time when the biological image is generated are associated with each other in advance.

An example of the situation identifying database is schematically shown in FIG. 5. As schematically shown in FIG. 5, situation-associated data in which a variety of information and a situation like the above are associated in advance are stored in the situation identifying database stored in the memory unit 209 according to the present embodiment or the like. The data format of such situation-associated data is not particularly limited; for example, a variety of information and a situation like the above may be recorded in a data format such as a look-up table. By referring to situation-associated data while using an acquired variety of information like the above, the situation identifying unit 211 can identify the situation corresponding to the acquired variety of information.

For example, in the case where reference to a variety of information like the above provides information that an energy device such as an electric scalpel is in operation, information that a smoke extraction apparatus is in operation, or the like, the situation identifying unit 211 may refer to situation-associated data while focusing attention on information like the above, and can thereby identify the fact that the visibility of the visual field is reduced by smoke or mist generated due to the energy device.

Further, information concerning the absorption coefficient or the spectral reflectance of an organ and a biological substance existing in the interior of the living body may be stored in the situation identifying database. For example, as shown in FIG. 6, each biological substance existing in the interior of the living body has an absorption coefficient peculiar to the biological substance. Therefore, a biological substance existing in the obtained biological images can be detected by focusing attention on a captured image of the living body in a specific wavelength range included in the plurality of biological images. Further, each organ and each biological substance existing in the interior of the living body have its own peculiar spectral reflectance similarly to the absorption coefficient. Here, attention may be given to a captured image of the living body in a specific wavelength range included in the plurality of biological images, the light source characteristics of the light source unit 105 of the medical observation apparatus 10, the sensor characteristics of the imaging unit 107, etc., and thereby the spectral reflectance in the obtained biological images can be calculated. Thus, the situation identifying unit 211 can identify the situation at the time when the interior of the living body is observed by comparing the obtained information and the information concerning the spectral reflectance or the absorption coefficient recorded in advance.

For example, in the case where the spectral reflectance or the absorption coefficient corresponding to blood has been identified from the value of the spectral reflectance or the absorption coefficient by focusing attention on information like the above (in particular, a biological image itself, secondary information obtained from a biological image, or the like), the situation identifying unit 211 can identify the fact that there is a blood vessel and possibly bleeding has occurred. Further, in the case where data corresponding to water have been detected by focusing attention on information like the above (in particular, a biological image itself, secondary information obtained from a biological image, or the like), the situation identifying unit 211 can infer that mist is generated in association with the use of an energy device.

Further, image information concerning an organ existing in the interior of the living body, a medical instrument used for medical practice, etc. may be stored in the situation identifying database. An organ, various medical instruments such as a blood flow obstruction medical instrument or a blood vessel anastomosis medical instrument, etc. existing in the biological images can be detected by performing image recognition on a biological image obtained from the medical observation apparatus 10 using the pieces of image information mentioned above. Thereby, the situation identifying unit 211 can infer the surgical site, the surgical situation, etc. The image recognition processing performed by the situation identifying unit 211 is not particularly limited, and various known image recognition processings such as pattern recognition and recognition by machine learning may be used as appropriate.

Other than various data like the above, various data for situation inference for inferring the situation may be stored in the situation identifying database as appropriate.

On thus identifying the situation at the time when the interior of the living body is observed while using the situation identifying database etc. as appropriate, the situation identifying unit 211 outputs situation information concerning the identified situation to the recommendation unit 213 in a later stage.

A situation identifying database like that shown in FIG. 5 may be updated via various networks and external memory devices as appropriate. The situation identifying unit 211 may be configured such that the situation identifying database is automatically updated by known machine learning processing or the like.

The recommendation unit 213 is formed of, for example, a CPU, a ROM, a RAM, etc. On the basis of a plurality of biological images generated by the medical observation apparatus 10 and situation information outputted from the situation identifying unit 211 concerning the situation at the time when the interior of the living body is observed, the recommendation unit 213 decides on at least one of the plurality of biological images or at least one of images generated from the plurality of biological images as a recommended image in accordance with the situation mentioned above. Further, the recommendation unit 213 recommends the decided on recommended image to the user of the medical observation apparatus 10.

More specifically, it is preferable that the recommendation unit 213 recommend a recommended image in accordance with the situation to the user with reference to a recommended image database in which situations at the time when the interior of the living body is observed and the type of the recommended image that can be presented at the time of each situation are associated with each other in advance.

An example of the recommended image database is schematically shown in FIG. 7. As schematically shown in FIG. 7, situations at the time when the interior of the living body is observed and the type of the recommended image that can be presented at the time of each situation are recorded while being associated with each other in the recommended image database stored in the memory unit 209 according to the present embodiment or the like. In the case where the fact that a certain situation (situation A) has occurred is described in the situation information outputted from the situation identifying unit 211, the recommendation unit 213 may refer to the item related to situation A in the recommended image database, and can decide on the recommendation of a near-infrared image as a recommended image, for example.

In the case where a plurality of recommended images are associated with a certain situation in the recommended image database, the recommendation unit 213 preferably recommends all the associated recommended images, rather than recommending the most suitable one from among the plurality of recommended images. In the case where a plurality of situations that possibly have occurred are listed in the situation information outputted from the situation identifying unit 211, the recommendation unit 213 preferably recommends recommended images corresponding to all the situations described in the situation information, rather than recommending a recommended image related to one of the plurality of situations. This is because it is preferable that the decision of what recommended image to use be made by the user of the medical observation apparatus 10 (that is, a doctor performing an operation or others).

On deciding on a recommended image to be recommended to the user of the medical observation apparatus 10, the recommendation unit 213 outputs information concerning the decided on recommended image to the output processing unit 205.

The information concerning the recommended image is not particularly limited, and may be, for example, at least one of text information showing the type of the recommended image and a thumbnail image of the recommended image. The output processing unit 205 causes the information concerning the recommended image to be outputted to the user of the medical observation apparatus 10 or the manipulator of the information processing apparatus 20. Thereby, the user of the medical observation apparatus 10 or the manipulator of the information processing apparatus 20 can decide whether to use the presented recommended image or not on the spot. Further, the output processing unit 205 may present the information concerning the recommended image to the user of the medical observation apparatus 10 or the manipulator of the information processing apparatus 20 using a means other than characters or images, such as sound or vibration.

On deciding on the type of the recommended image to be recommended to the user of the medical observation apparatus 10, the recommendation unit 213 requests the recommended image generation unit 215 in a later stage to generate the decided on recommended image, as necessary.

In the case where the user of the medical observation apparatus 10 has chosen reference to a recommended image, the recommendation unit 213 causes the chosen recommended image to be appropriately presented to the user of the medical observation apparatus 10 via the output processing unit 205. The recommendation unit 213 may assist the choice by the user of the medical observation apparatus 10 or others by recording the history of the result of choice by the user of the medical observation apparatus 10 or others in the memory unit 209 or the like as appropriate and causing also the history information to be displayed at the time of the next recommendation.

A recommended image database like that shown in FIG. 7 may be updated via various networks or external memory devices as appropriate. The recommendation unit 213 may be configured such that the recommended image database is automatically updated by known machine learning processing or the like.

The recommended image generation unit 215 is formed of, for example, a CPU, a ROM, a RAM, etc. The recommended image generation unit 215 uses at least one of at least part of the plurality of biological images and an image in which secondary information generated by analyzing at least one of the plurality of biological images is visualized, and generates a recommended image to be recommended by the recommendation unit 213.

For example, in the case where an observation image in a specific wavelength range (for example, the near-infrared region) is recommended as a recommended image by the recommendation unit 213, the recommended image generation unit 215 may use a captured image of the living body in the corresponding wavelength range out of the plurality of biological images, and can thereby generate an observation image, a thumbnail image thereof, or the like in the relevant wavelength range as a recommended image. Further, in the case where oxygen saturation-visualized information in which the distribution of oxygen saturation identifiable as secondary information of a biological image is visualized, such as that shown by the database of FIG. 7, is a recommended image, the secondary information may be used to generate a relevant recommended image, a thumbnail image thereof, or the like. Other than these images, a known method such as the principle of NBI may be used, and thereby various known images such as a blood vessel-highlighted image in which the existence of a blood vessel is highlighted and an image showing the manner of blood flowing, a thumbnail image thereof, or the like can be generated as appropriate.

Further, attention is given to the case where a captured image of the living body in the visible light region and a captured image of the living body in the near-infrared region (for example, a fluorescence image in the near-infrared region or the like) are included as a plurality of biological images. Here, in the fluorescence image in the near-infrared region, in many cases the portion corresponding to fluorescence is displayed in a predetermined color tone and the portion not corresponding to fluorescence (the portion in which the luminance value is zero or close to zero) is displayed in black. Even when such a fluorescence image is presented as a recommended image, it is highly likely that the positional relationship between internal organs etc. is hard to understand. Thus, the recommended image generation unit 215 first changes the color tone of the area in the captured image of the living body in the near-infrared region where light in the near-infrared region has been detected (for example, the portion corresponding to fluorescence) to a predetermined color tone (for example, green color, which is a color tone not existing in the living body), and changes the luminance value of the area where light in the near-infrared region has not been detected to zero. After that, the recommended image generation unit 215 may generate a superimposed image in which the captured image of the living body in the near-infrared region after change is superimposed on the captured image of the living body in the visible light region, and may use the superimposed image as a recommended image.

In the above, an example of the function of the information processing apparatus 20 according to the present embodiment is described. Each structural element mentioned above may be configured using a general-purpose member or circuit, or may be configured using a hardware member dedicated to the function of each structural element. It is also possible for all the functions of the structural elements to be performed by a CPU or the like. Thus, the configuration for use may be altered in accordance with the technical level on every occasion of implementing the present embodiment, as appropriate.

A computer program for performing each function of the information processing apparatus according to the present embodiment like the above may be created and mounted on a personal computer or the like. Further, a computer-readable recording medium in which such a computer program is stored can be provided. The recording medium is, for example, a magnetic disk, an optical disk, a magneto-optical disk, a flash memory, or the like. The computer program mentioned above may be distributed via a network without using a recording medium, for example.

With Regard to Examples of Presentation of Recommended Image

Next, methods for presenting a recommended image decided on by the recommendation unit 213 are briefly described with reference to FIG. 8 and FIG. 9. FIG. 8 schematically shows examples of the display screen viewed by the user of the medical observation apparatus 10 or the manipulator of the information processing apparatus 20, such as the display unit 109 of the medical observation apparatus 10 or a display device of the information processing apparatus 20 (not shown).

In general, when various medical practices such as an operation are performed, it is probable that, as schematically shown in the diagram at the upper left of FIG. 8, a captured image of the living body in the visible light region (a visible light image) is displayed as normal display on the display screen by the control unit 101 of the medical observation apparatus 10 or the display control unit 207 of the information processing apparatus 20. Here, when a recommended image in accordance with the situation is proposed by the recommendation unit 213, for example as schematically shown in the diagram at the upper right of FIG. 8, the recommendation unit 213 may cause text information showing the type of the recommended image to be displayed so as to be superimposed on the visible light image via the output processing unit 205. Alternatively, for example as schematically shown in the diagram at the lower left of FIG. 8, the recommendation unit 213 may cause, instead of only text information, an text image showing the type of the recommended image and a thumbnail image of the recommended image to be displayed together, or may cause a thumbnail image of the recommended image to be singly displayed in the display format of what is called picture-in-picture. Alternatively, as schematically show in the diagram at the lower right of FIG. 8, the recommendation unit 213 may cause a display region for displaying information concerning recommended images to be provided around the visible light image, and may cause text information showing the types of the recommended images, thumbnail images of the recommended images, text information describing the recommended images, etc. to be displayed together in the display region.

By generating a display screen like those shown in FIG. 8, the user of the medical observation apparatus 10 is enabled to choose whether to cause a recommended image to be displayed on the display screen or not.

Further, instead of using one display screen like those shown in FIG. 8, as schematically shown in FIG. 9 a recommended image like the above and information related to the recommended image may be caused to be displayed on, not a main monitor on which a visible light image is displayed, but a sub-monitor provided separately from the main monitor.

The display of information concerning recommended images like those shown in FIG. 8 and FIG. 9 may be caused to disappear every time when the user of the medical observation apparatus 10 does not choose the use of the recommended image. Further, the display of information concerning a recommended image like those shown in FIG. 8 and FIG. 9 may be caused to automatically disappear after a certain time has elapsed. Further, the display of information concerning a recommended image like those shown in FIG. 8 and FIG. 9 may be recorded by various methods so that it can be checked by reproduction during the operation or after the operation.

On the other hand, in the case where, based on the display of information concerning a recommended image like those shown in FIG. 8 and FIG. 9, the user of the medical observation apparatus 10 has chosen the use of the recommended image, the chosen recommended image is displayed on the display screen. The timing of the re-switching from the recommended image to the normal visible light image is not particularly limited, and the re-switching is performed in accordance with the user manipulation etc. by the user of the medical observation apparatus 10, as appropriate.

In the above, methods for presenting a recommended image decided on by the recommendation unit 213 are briefly described.

With Regard to Specific Examples of Recommended Image

In the following, the recommended image is briefly described with some specific examples.

Case 1

In the case where, for example, bleeding has occurred during an operation with the medical observation apparatus 10, it is important that the user of the medical observation apparatus 10 quickly find the bleeding point and perform hemostasic treatment. However, when there is a large amount of bleeding, there is a case where the surroundings are bloodstained and it is difficult to look for the bleeding point.

In this event, it is assumed that blood has been recognized and the situation of ongoing bleeding has been identified by situation identifying processing by the situation identifying unit 211 (for example, the processing of analyzing a captured image in a specific wavelength range). On the other hand, the absorption coefficient of blood is low in the near-infrared region as shown in FIG. 6, and light in the near-infrared region is transmitted through blood. Thus, the recommendation unit 213 refers to the recommended image database etc., and selects, as a recommended image, an observation image in a wavelength range in which the absorption coefficient of blood is relatively low. By using such a recommended image, it becomes easy for the user of the medical observation apparatus 10 to visually identify the surface of the living body that is buried in blood and hard to see and to find the bleeding point.

Case 2

When, for example, an energy device such as an electric scalpel is used, there is a case where the interior of the body cavity is covered with surgical smoke or mist and the visibility is worsened.

In this event, it is assumed that the situation of surgical smoke or mist being generated has been identified by situation identifying processing by the situation identifying unit 211 (for example, the processing of analyzing a captured image in a specific wavelength range, or information concerning the operating situation of various devices). In this case, the recommendation unit 213 refers to the recommended image database etc., and selects, as a recommended image, an observation image in the near-infrared region in which the absorption coefficient of surgical smoke and mist is relatively low. By using such a recommended image, the user of the medical observation apparatus 10 can continue the medical practice without suspending the working due to surgical smoke or mist.

Further, in the case where it has been assessed that, after the lapse of a certain period of time of a situation like the above, the smoke extraction device etc. operate normally and thereby the surgical smoke, mist, and the like have disappeared, the recommendation unit 213 may switch the display from the observation image in the near-infrared region to the normal observation image in the visible light region. Thus, the user of the medical observation apparatus 10 can continue the medical practice using a familiar image.

Case 3

When, for example, cutting off a blood vessel safely, the doctor completely obstructs the blood by attaching a blood flow obstruction medical instrument such as a clip to the blood vessel, and then cuts off the blood vessel with a predetermined surgical instrument. In this event, there is a case where the attachment of the blood flow obstruction medical instrument such as a clip is insufficient and the blood flow is not completely obstructed. If the blood vessel is cut off in the situation where the blood flow is not completely obstructed, unintentional bleeding occurs. Similarly, it is necessary to appropriately anastomose the blood vessels or tissues using a blood vessel anastomosis medical instrument such as a stapler and to check whether the blood flow is resumed or not.

In this event, in the case where situation information that the blood flow obstruction medical instrument or the blood vessel anastomosis medical instrument is detected has been generated by situation identifying processing by the situation identifying unit 211 (for example, the image recognition processing of the clip, the stapler, or the like), the recommendation unit 213 may calculate the oxygen saturation as secondary information based on a biological image by a known method, and may use, as a recommended image, an image in which the distribution of oxygen saturation is visualized.

Instead of an image in which the distribution of oxygen saturation is visualized, a captured image of the living body in the near-infrared region corresponding to the distribution of blood may be used as a recommended image. For example, a fluorescent reagent called indocyanine green (ICG) has the property of binding to plasma protein in blood and thereby emitting fluorescence of 830 nanometers by means of excitation light of 760 nanometers. Thus, in the case where a situation like the above is grasped, the recommendation unit 213 may first recommend the use of the fluorescent reagent to the doctor who is the user of the medical observation apparatus 10, and may recommend a near-infrared image at a wavelength of around 830 nanometers generated due to the fluorescent reagent, as an observation image in the near-infrared region corresponding to the distribution of blood.

Case 4

There may be a case where, for example, during an operation with the medical observation apparatus 10 the user of the medical observation apparatus 10 wants to know information concerning the running of a blood vessel or the depth of a blood vessel; but a common captured image in the visible light region may not allow such information to be sufficiently obtained.

In this event, when the fact that a blood vessel exists in a biological image is identified by situation identifying processing by the situation identifying unit 211 (for example, the processing of analyzing a captured image in a specific wavelength range), the recommendation unit 213 may use a similar means to the principle of NBI, and may recommend an image in a wavelength range suitable for the visual identification of the blood vessel as a blood vessel-highlighted image.

In the above, the recommended image is briefly described with some specific examples; but the recommended image in the information processing apparatus 20 according to the present embodiment is not limited to the examples described above, and various known images may be used as the recommended image.

<With Regard to Information Processing Method>

Figure 10:
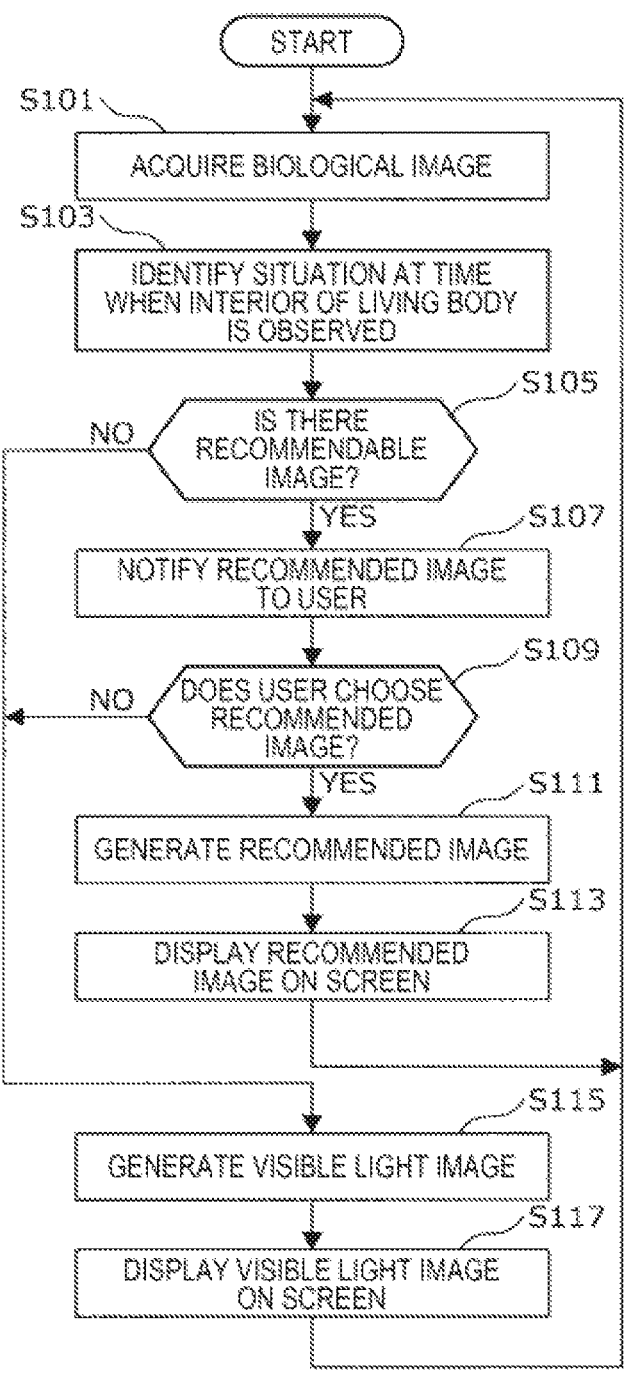
FIG. 10 is a flow chart showing an example of the flow of an information processing method according to the embodiment.

Next, a flow of an information processing method according to the present embodiment is briefly described with reference to FIG. 10. FIG. 10 is a flow chart showing an example of the flow of the information processing method according to the present embodiment.

In the information processing method according to the present embodiment, first, biological images are generated by the medical observation apparatus 10, and are outputted to the information processing apparatus 20. On acquiring the data of the biological images outputted from the medical observation apparatus 10 (step S101), the information acquisition unit 201 of the information processing apparatus 20 outputs the acquired data to the image recommendation processing unit 203.

The situation identifying unit 211 of the image recommendation processing unit 203 identifies the situation at the time when the interior of the living body is observed by a method like that described above (step S103), and outputs situation information concerning the identified situation to the recommendation unit 213.

The recommendation unit 213 uses the situation information outputted from the situation identifying unit 211 etc., and assesses whether there is an image recommendable to the user of the medical observation apparatus 10 or others or not (step S105). In the case where there is no recommendable image (step S105-NO), step S115 described later is performed. On the other hand, in the case where there is a recommendable image (step S105-YES), the recommendation unit 213 causes information concerning the recommended image to be notified to the user of the medical observation apparatus 10 by a method like that described above (step S107).

Here, in the case where the user of the medical observation apparatus 10 or others have not chosen the recommended image (step S109-NO), step S115 described later is performed. On the other hand, in the case where the user of the medical observation apparatus 10 or others have chosen the recommended image (step S109-YES), the recommended image is generated by the recommended image generation unit 215 as necessary (step S111), and the output processing unit 205, the control unit 101 of the medical observation apparatus 10, etc. work in cooperation; thereby, the recommended image is displayed on a screen (step S113). After that, the procedure returns to step S101, and the information processing method according to the present embodiment is continued.

On the other hand, in the case where in step S105 it has been assessed that there is no recommendable image and in the case where in step S109 the recommended image has not been chosen, a captured image of the living body in the visible light region is generated (step S115), and the output processing unit 205, the control unit 101 of the medical observation apparatus 10, etc. work in cooperation; thereby, the visible light image is displayed on a screen (step S117). After that, the procedure returns to step S101, and the information processing method according to the present embodiment is continued.

In the above, a flow of the information processing method according to the present embodiment is briefly described with reference to FIG. 10.

<Hardware Configuration>

Figure 11:
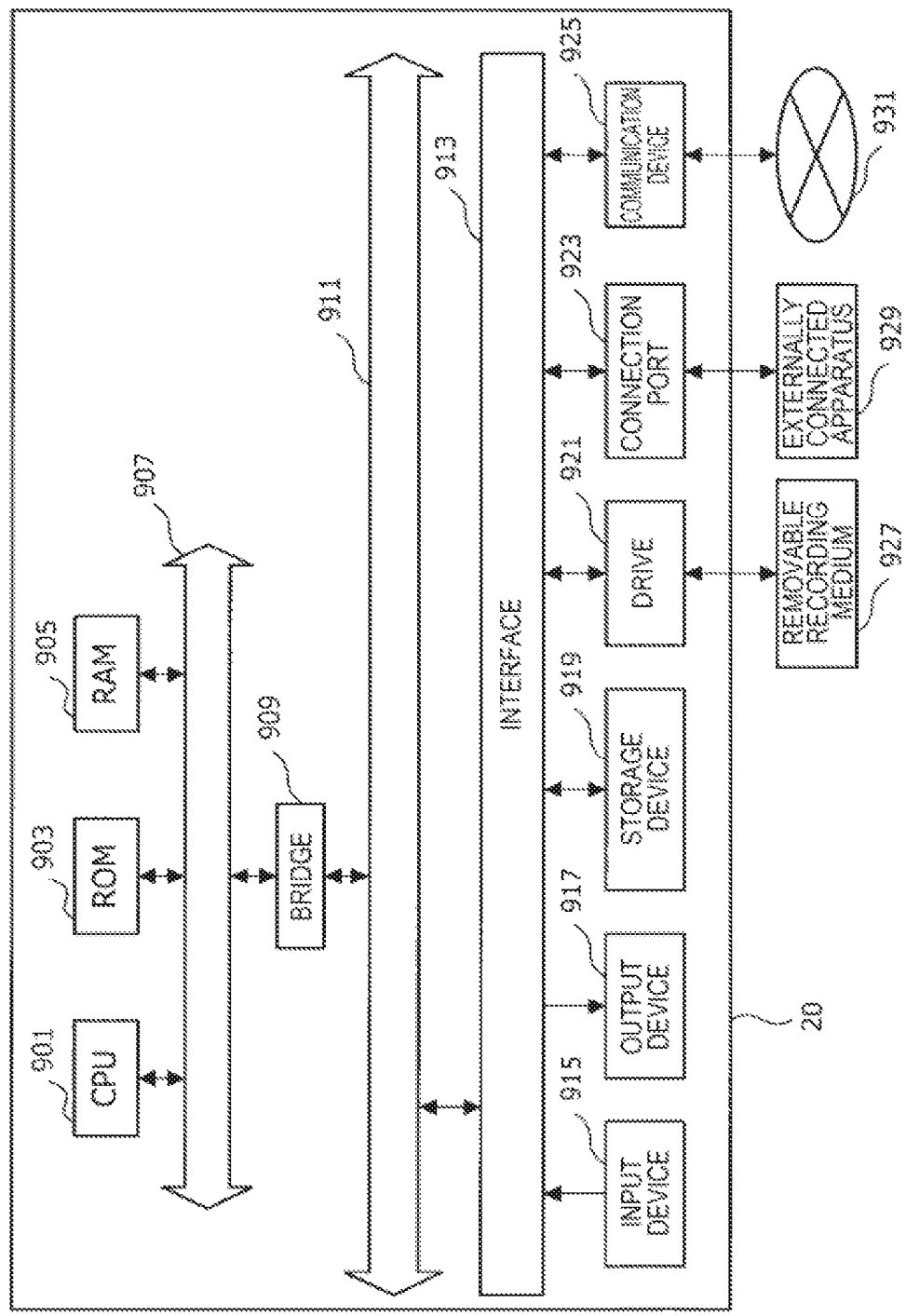
FIG. 11 is a block diagram showing an example of the hardware configuration of the information processing apparatus according to the embodiment.

Next, the hardware configuration of the information processing apparatus 20 according to the embodiment of the present disclosure will be described in detail with reference to FIG. 11. FIG. 11 is a block diagram for illustrating the hardware configuration of the information processing apparatus 20 according to the embodiment of the present disclosure.

The information processing apparatus 20 mainly includes a CPU 901, a ROM 903, and a RAM 905. Furthermore, the information processing apparatus 20 also includes a host bus 907, a bridge 909, an external bus 911, an interface 913, an input device 915, an output device 917, a storage device 919, a drive 921, a connection port 923, and a communication device 925.

The CPU 901 serves as an arithmetic processing apparatus and a control device, and controls the overall operation or a part of the operation of the information processing apparatus 20 according to various programs recorded in the ROM 903, the RAM 905, the storage device 919, or a removable recording medium 927. The ROM 903 stores programs, operation parameters, and the like used by the CPU 901. The RAM 905 primarily stores programs that the CPU 901 uses and parameters and the like varying as appropriate during the execution of the programs. These are connected with each other via the host bus 907 configured from an internal bus such as a CPU bus or the like.

The host bus 907 is connected to the external bus 911 such as a PCI (Peripheral Component Interconnect/Interface) bus via the bridge 909.

The input device 915 is an operation means operated by a user, such as a mouse, a keyboard, a touch panel, buttons, a switch and a lever. Also, the input device 915 may be a remote control means (a so-called remote control) using, for example, infrared light or other radio waves, or may be an externally connected apparatus 929 such as a mobile phone or a PDA conforming to the operation of the information processing apparatus 20. Furthermore, the input device 915 generates an input signal based on, for example, information which is input by a user with the above operation means, and is configured from an input control circuit for outputting the input signal to the CPU 901. The user can input various data to the information processing apparatus 20 and can instruct the information processing apparatus 20 to perform processing by operating this input apparatus 915.

The output device 917 is configured from a device capable of visually or audibly notifying acquired information to a user. Examples of such device include display devices such as a CRT display device, a liquid crystal display device, a plasma display device, an EL display device and lamps, audio output devices such as a speaker and a headphone, a printer, a mobile phone, a facsimile machine, and the like. For example, the output device 917 outputs a result obtained by various processings performed by the information processing apparatus 20. More specifically, the display device displays, in the form of texts or images, a result obtained by various processes performed by the information processing apparatus 20. On the other hand, the audio output device converts an audio signal such as reproduced audio data and sound data into an analog signal, and outputs the analog signal.

The storage device 919 is a device for storing data configured as an example of a storage unit of the information processing apparatus 20 and is used to store data. The storage device 919 is configured from, for example, a magnetic storage device such as a HDD (Hard Disk Drive), a semiconductor storage device, an optical storage device, or a magneto-optical storage device. This storage device 919 stores programs to be executed by the CPU 901, various data, and various data obtained from the outside.

The drive 921 is a reader/writer for recording medium, and is embedded in the information processing apparatus 20 or attached externally thereto. The drive 921 reads information recorded in the attached removable recording medium 927 such as a magnetic disk, an optical disk, a magneto-optical disk, or a semiconductor memory, and outputs the read information to the RAM 905. Furthermore, the drive 921 can write in the attached removable recording medium 927 such as a magnetic disk, an optical disk, a magneto-optical disk, or a semiconductor memory. The removable recording medium 927 is, for example, a DVD medium, an HD-DVD medium, or a Blu-ray (registered trademark) medium. The removable recording medium 927 may be a CompactFlash (CF; registered trademark), a flash memory, an SD memory card (Secure Digital Memory Card), or the like. Alternatively, the removable recording medium 927 may be, for example, an IC card (Integrated Circuit Card) equipped with a non-contact IC chip or an electronic appliance.

The connection port 923 is a port for allowing devices to directly connect to the information processing apparatus 20. Examples of the connection port 923 include a USB (Universal Serial Bus) port, an IEEE1394 port, a SCSI (Small Computer System Interface) port, and the like. Other examples of the connection port 923 include an RS-232C port, an optical audio terminal, an HDMI (High-Definition Multimedia Interface) port, and the like. By the externally connected apparatus 929 connecting to this connection port 923, the information processing apparatus 20 directly obtains various data from the externally connected apparatus 929 and provides various data to the externally connected apparatus 929.

The communication device 925 is a communication interface configured from, for example, a communication device for connecting to a communication network 931. The communication device 925 is, for example, a wired or wireless LAN (Local Area Network), Bluetooth (registered trademark), a communication card for WUSB (Wireless USB), or the like. Alternatively, the communication device 925 may be a router for optical communication, a router for ADSL (Asymmetric Digital Subscriber Line), a modem for various communications, or the like. This communication device 925 can transmit and receive signals and the like in accordance with a predetermined protocol such as TCP/IP on the Internet and with other communication devices, for example. The communication network 931 connected to the communication device 925 is configured from a network and the like, which is connected via wire or wirelessly, and may be, for example, the Internet, a home LAN, infrared communication, radio wave communication, satellite communication, or the like.

Heretofore, an example of the hardware configuration capable of realizing the functions of the information processing apparatus 20 according to the embodiment of the present disclosure has been shown. Each of the structural elements described above may be configured using a general-purpose material, or may be configured from hardware dedicated to the function of each structural element. Accordingly, the hardware configuration to be used can be changed as appropriate according to the technical level at the time of carrying out the present embodiment.

It should be understood by those skilled in the art that various modifications, combinations, sub-combinations and alterations may occur depending on design requirements and other factors insofar as they are within the scope of the appended claims or the equivalents thereof.

Further, the effects described in this specification are merely illustrative or exemplified effects, and are not limitative. That is, with or in the place of the above effects, the technology according to the present disclosure may achieve other effects that are clear to those skilled in the art based on the description of this specification.

Additionally, the present technology may also be configured as below.

(1)
A medical information processing apparatus comprising:
processing circuitry configured to, based on surgical situation information concerning surgical characteristics at a time of observing an interior of a living body, select at least one of a plurality of biological images each having a different wavelength range or at least one of secondary images generated from the plurality of biological images each having a different wavelength range, as a recommended image.

(2)
The medical information processing apparatus according to (1),
wherein the plurality of biological images include at least a captured image of the living body in a visible light region, and
wherein the processing circuitry is further configured to perform display control of a display screen on which the plurality of biological images are displayed, and switch the display screen to display the captured image of the living body in the visible light region and the recommended image on the display screen in response to a manual input.

(3)
The medical information processing apparatus according to (1),
wherein the processing circuitry is further configured to access a recommended image database which associates different surgical characteristics at the time of observing the interior of the living body with different recommended images, and selects the recommended image based on respective surgical characteristics.

(4)
The medical information processing apparatus according to (1), wherein the processing circuitry is further configured to generate the recommended image using at least one of:
at least some of the plurality of biological images and secondary information generated by analyzing at least one of the plurality of biological images.

(5)
The medical information processing apparatus according to (4),
wherein the plurality of biological images include a first captured image of the living body in a visible light region and a second captured image of the living body in a near-infrared region, and
the processing circuitry is further configured to change a color tone of an area of the second captured image in which light, in the near-infrared region, has been detected to a predetermined color tone in the display.

(6)
The medical information processing apparatus according to (1),
wherein the plurality of biological images include at least a captured image of the living body in a visible light region, and
the processing circuitry instructs display of information regarding the recommended image on a display screen on which the captured image of the living body in the visible light region is also displayed.

(7)
The medical information processing apparatus according to (6), wherein the information concerning the recommended image is at least one of text information showing a type of the recommended image and a thumbnail image of the recommended image.

(8)
The medical information processing apparatus according to (1), wherein the processing circuitry is configured to instruct display of the recommended image on a first display screen different from a second display screen on which a captured image of the living body in a visible light region out of the plurality of biological images, is displayed.

(9)
The medical information processing apparatus according to (1), wherein the processing circuitry is further configured to identify the surgical characteristics at the time that the interior of the living body is observed based on at least one of:
settings of a medical observation apparatus used to observe the interior of the living body, characteristics of the medical observation apparatus, an operating state of the medical observation apparatus or a peripheral device cooperating with the medical observation apparatus, the plurality of biological images, and secondary information generated based on the plurality of biological images.

(10)
The medical information processing apparatus according to (9),
wherein the processing circuitry is further configured to identify the surgical characteristics at the time that the interior of the living body is observed with reference to a surgical characteristics identification database in which at least one of:
settings of a medical observation apparatus used to observe the interior of the living body, characteristics of the medical observation apparatus, an operating state of the medical observation apparatus or a peripheral device cooperating with the medical observation apparatus, the plurality of biological images, and secondary information generated based on the plurality of biological images, is associated with surgical characteristics in effect at a time that the plurality of biological images are generated.

(11)
The medical information processing apparatus according to (10),
wherein information concerning a spectral reflectance or an absorption coefficient of an organ and a biological substance existing in the interior of the living body is further recorded in the surgical characteristics identification database, and
wherein the processing circuitry is further configured to identify the surgical characteristics at the time that the interior of the living body is being observed based on the information concerning the spectral reflectance or the absorption coefficient of the organ and the biological substance existing in the interior of the living body.

(12)
The medical information processing apparatus according to (10),
wherein first image information concerning an organ in the interior of the living body or a medical instrument is further recorded in the surgical characteristics identification database, and
the processing circuitry is further configured to identify the surgical characteristics at the time when the interior of the living body is observed, based on the first image information.

(13)
The medical information processing apparatus according to (1),
wherein a first captured image of the living body in a visible light region and a second captured image of the living body in a near-infrared region, are included in the plurality of biological images, and
the processing circuitry is configured to select the first captured image of the living body in the near-infrared region as the recommended image in a case that the surgical characteristics include that blood is detected.

(14)
The medical information processing apparatus according to (1),
wherein at least a first captured image of the living body in a visible light region and a second captured image of the living body in a near-infrared region are included in the plurality of biological images, and
wherein the processing circuitry is configured to select the second captured image of the living body in the near-infrared region as the recommended image in a case that the surgical characteristics include that smoke or mist is detected or a medical energy device is in use.

(15)
The medical information processing apparatus according to (14),
wherein the processing circuitry is configured to instruct a display screen to be switched from the recommended image to the first captured image of the living body in the visible light region in a case that the surgical characteristics include that no smoke or mist is detected and that use of the medical energy device is finished.

(16)
The medical information processing apparatus according to (1),
wherein the processing circuitry is configured to select, as the recommended image, an image of the secondary images in which a distribution of oxygen saturation generated as secondary information, based on the plurality of biological images, is visualized, or a captured image of the living body in a near-infrared region of the plurality of biological images, that corresponds to a distribution of blood, in a case that the surgical characteristics include that a blood flow obstruction medical instrument or a blood vessel anastomosis medical instrument, is detected.

(17)
The medical information processing apparatus according to (1),
wherein on the processing circuitry is configured to select a captured image of the living body of the plurality of biological images having a wavelength range permitting visual identification of a blood vessel, as the recommended image in a case that the surgical characteristics include that an existence of a blood vessel is detected.

(18)
The medical information processing apparatus according to (1), further comprising:
a medical observation apparatus that includes a multispectral sensor including at least a pixel configured to detect intensities of light in a plurality of wavelength ranges at one time while distinguishing intensities for each wavelength range,
wherein a biological image for each of the plurality of wavelength ranges is generated from an output result of the multispectral sensor as the plurality of biological images.

(19)
The medical information processing apparatus according to (1), further comprising:
a medical observation apparatus that includes a plurality of imaging elements corresponding to specific wavelength ranges,
wherein a biological image for each of a plurality of wavelength ranges is generated from an output result of the imaging elements as the plurality of biological images.

(20)
The medical information processing apparatus according to (1), further comprising:
a medical observation apparatus that generates a biological image for each of a plurality of wavelength ranges as the plurality of biological images, by performing imaging while switching a wavelength range of light that forms an image on an imaging element included in the medical observation apparatus.

(21)
The information processing apparatus according to (1), further comprising:
a medical observation apparatus that is a medical endoscope or a medical microscope.

(22)
A medical information processing method including:
selecting, based on surgical situation information concerning surgical characteristics at a time of observing an interior of a living body, at least one of a plurality of biological images each having a different wavelength range or at least one of secondary images generated from the plurality of biological images each having a different wavelength range, as a recommended image.

(23)
A non-transitory computer readable medium having stored therein a program that when executed by a computer causes the computer to execute a medical information processing method, comprising:
selecting, based on surgical situation information concerning surgical characteristics at a time of observing an interior of a living body, at least one of a plurality of biological images each having a different wavelength range or at least one of secondary images generated from the plurality of biological images each having a different wavelength range, as a recommended image.

(24)
A medical observation system including:
a medical observation apparatus including
first processing circuitry configured to generate a plurality of biological images by capturing images of an interior and exterior of a living body in a plurality of wavelength ranges; and
an information processing apparatus including
second processing circuitry configured to, based on surgical situation information concerning surgical characteristics at a time of observing the interior of the living body, select at least one of the plurality of biological images having different wavelength ranges or at least one of secondary images generated from the plurality of biological images, as a recommended image.

REFERENCE SIGNS LIST 1 medical observation system
10 medical observation apparatus
20 information processing apparatus
101 control unit (processing circuitry)
103 observation unit
105 light source unit (light source)
107 imaging unit
109 display unit (display)
201 information acquisition unit (processing circuitry)
203 image recommendation processing unit (processing circuitry)
205 output processing unit (processing circuitry)
207 display control unit (processing circuitry)
209 memory unit (memory)
211 situation identifying unit (processing circuitry)
213 recommendation unit (processing circuitry)
215 recommended image generation unit (processing circuitry)

The invention claimed is:

1. A medical information processing apparatus comprising:
processing circuitry configured to:
select at least one of a plurality of biological images each having a different wavelength range or at least one of secondary images generated from the plurality of biological images each having a different wavelength range, as a recommended image for use while performing a medical procedure, based on surgical situation information concerning surgical characteristics at a time of observing an interior of a living body, wherein the plurality of biological images comprise a captured image of the living body in the visible light region; and
display the recommended image and the captured image of the living body in the visible light region on a display screen,
wherein the recommended image is a particular secondary image generated by adding a color to at least a portion of one of the plurality of biological images.

2. The medical information processing apparatus according to claim 1,
wherein the processing circuitry is further configured to perform display control of the display screen on which the plurality of biological images are displayed, and
switch the display screen to display the captured image of the living body in the visible light region and the recommended image on the display screen in response to a manual input.

3. The medical information processing apparatus according to claim 1,
wherein the processing circuitry is further configured to access a recommended image database which associates different surgical characteristics at the time of observing the interior of the living body with different recommended images, and selects the recommended image based on respective surgical characteristics.

4. The medical information processing apparatus according to claim 1, wherein the processing circuitry is further configured to generate the recommended image using at least one of:
at least some of the plurality of biological images and secondary information generated by analyzing at least one of the plurality of biological images.

5. The medical information processing apparatus according to claim 4,
wherein the plurality of biological images include a second captured image of the living body in a near-infrared region, and
the processing circuitry is further configured to change a color tone of an area of the second captured image in which light, in the near-infrared region, has been detected to a predetermined color tone in the display.

6. The medical information processing apparatus according to claim 1,
wherein the processing circuitry instructs display of information regarding the recommended image on a display screen on which the captured image of the living body in the visible light region is also displayed.

7. The medical information processing apparatus according to claim 6, wherein the information concerning the recommended image is at least one of text information showing a type of the recommended image and a thumbnail image of the recommended image.

8. The medical information processing apparatus according to claim 1, wherein the processing circuitry is configured to instruct display of the recommended image on a first display screen different from a second display screen on which a captured image of the living body in a visible light region out of the plurality of biological images, is displayed.

9. The medical information processing apparatus according to claim 1, wherein the processing circuitry is further configured to identify the surgical characteristics at the time that the interior of the living body is observed based on at least one of:
settings of a medical observation apparatus used to observe the interior of the living body, characteristics of the medical observation apparatus, an operating state of the medical observation apparatus or a peripheral device cooperating with the medical observation apparatus, the plurality of biological images, and secondary information generated based on the plurality of biological images.

10. The medical information processing apparatus according to claim 9,
wherein the processing circuitry is further configured to identify the surgical characteristics at the time that the interior of the living body is observed with reference to a surgical characteristics identification database in which at least one of:
settings of a medical observation apparatus used to observe the interior of the living body, characteristics of the medical observation apparatus, an operating state of the medical observation apparatus or a peripheral device cooperating with the medical observation apparatus, the plurality of biological images, and secondary information generated based on the plurality of biological images, is associated with surgical characteristics in effect at a time that the plurality of biological images are generated.

11. The medical information processing apparatus according to claim 10,
wherein information concerning a spectral reflectance or an absorption coefficient of an organ and a biological substance existing in the interior of the living body is further recorded in the surgical characteristics identification database, and
wherein the processing circuitry is further configured to identify the surgical characteristics at the time that the interior of the living body is being observed based on the information concerning the spectral reflectance or the absorption coefficient of the organ and the biological substance existing in the interior of the living body.

12. The medical information processing apparatus according to claim 10,
wherein first image information concerning an organ in the interior of the living body or a medical instrument is further recorded in the surgical characteristics identification database, and
the processing circuitry is further configured to identify the surgical characteristics at the time when the interior of the living body is observed, based on the first image information.

13. The medical information processing apparatus according to claim 1,
wherein a second captured image of the living body in a near-infrared region is included in the plurality of biological images, and
the processing circuitry is configured to select the first captured image of the living body in the near-infrared region as the one of the plurality of biological images for generating the particular secondary image selected as the recommended image in a case that the surgical characteristics include that blood is detected.

14. The medical information processing apparatus according to claim 1,
wherein a second captured image of the living body in a near-infrared region is included in the plurality of biological images, and
wherein the processing circuitry is configured to select the second captured image of the living body in the near-infrared region as the one of the plurality of biological images for generating the particular secondary image selected as the recommended image in a case that the surgical characteristics include that smoke or mist is detected or a medical energy device is in use.

15. The medical information processing apparatus according to claim 14,
wherein the processing circuitry is configured to instruct a display screen to be switched from the recommended image to the first captured image of the living body in the visible light region in a case that the surgical characteristics include that no smoke or mist is detected and that use of the medical energy device is finished.

16. The medical information processing apparatus according to claim 1, wherein the processing circuitry is configured to select, as the recommended image, an image of the secondary images in which a distribution of oxygen saturation generated as secondary information, based on the plurality of biological images, is visualized, or a captured image of the living body in a near-infrared region of the plurality of biological images, that corresponds to a distribution of blood, in a case that the surgical characteristics include that a blood flow obstruction medical instrument or a blood vessel anastomosis medical instrument, is detected.

17. The medical information processing apparatus according to claim 1,
wherein on the processing circuitry is configured to select a captured image of the living body of the plurality of biological images having a wavelength range permitting visual identification of a blood vessel, as the one of the plurality of biological images for generating the particular secondary image selected as the recommended image in a case that the surgical characteristics include that an existence of a blood vessel is detected.

18. The medical information processing apparatus according to claim 1, further comprising:
a medical observation apparatus that includes a multi-spectral sensor including at least a pixel configured to detect intensities of light in a plurality of wavelength ranges at one time while distinguishing intensities for each wavelength range,
wherein a biological image for each of the plurality of wavelength ranges is generated from an output result of the multispectral sensor as the plurality of biological images.

19. The medical information processing apparatus according to claim 1, further comprising:
a medical observation apparatus that includes a plurality of imaging elements corresponding to specific wavelength ranges,
wherein a biological image for each of a plurality of wavelength ranges is generated from an output result of the imaging elements as the plurality of biological images.

20. The medical information processing apparatus according to claim 1, further comprising:
a medical observation apparatus that generates a biological image for each of a plurality of wavelength ranges as the plurality of biological images, by performing imaging while switching a wavelength range of light that forms an image on an imaging element included in the medical observation apparatus.

21. The medical information processing apparatus according to claim 1, further comprising:
a medical observation apparatus that is a medical endoscope or a medical microscope.

22. The medical information processing apparatus according to claim 1, wherein the one of the plurality of biological images used to generate the secondary image has an infrared wavelength.

23. The medical information processing apparatus according to claim 1, wherein the color is a predetermined color that does not exist in the living body.

24. A medical information processing method comprising:
selecting at least one of a plurality of biological images each having a different wavelength range or at least one of secondary images generated from the plurality of biological images each having a different wavelength range, as a recommended image for use while performing a medical procedure, based on surgical situation information concerning surgical characteristics at a time of observing an interior of a living body, wherein the plurality of biological images comprise a captured image of the living body in the visible light region; and
displaying the recommended image and the captured image of the living body in the visible light region on a display screen,
wherein the recommended image is a particular secondary image generated by adding a color to at least a portion of one of the plurality of biological images.

25. A non-transitory computer readable medium having stored therein a program that when executed by a computer causes the computer to execute a medical information processing method, comprising:
selecting at least one of a plurality of biological images each having a different wavelength range or at least one of secondary images generated from the plurality of biological images each having a different wavelength range, as a recommended image for use while performing a medical procedure, based on surgical situation information concerning surgical characteristics at a time of observing an interior of a living body, wherein the plurality of biological images comprise a captured image of the living body in the visible light region; and displaying the recommended image and the captured image of the living body in the visible light region on a display screen, wherein the recommended image is a particular secondary image generated by adding a color to at least a portion of one of the plurality of biological images.

26. A medical observation system comprising:

a medical observation apparatus including first processing circuitry configured to generate a plurality of biological images by capturing images of an interior and exterior of a living body in a plurality of wavelength ranges; and an information processing apparatus including second processing circuitry configured to select at least one of the plurality of biological images having different wavelength ranges or at least one of secondary images generated from the plurality of biological images, as a recommended image for performing a medical procedure, based on surgical situation information concerning surgical characteristics at a time of observing an interior of a living body, wherein the plurality of biological images comprise a captured image of the living body in the visible light region; and the second processing circuitry is configured to display the recommended image and the captured image of the living body in the visible light region on a display screen, wherein the recommended image is a particular secondary image generated by adding a color to at least a portion of one of the plurality of biological images.

* * * * *